US010011628B2

(12) United States Patent
Arnberg et al.

(10) Patent No.: US 10,011,628 B2
(45) Date of Patent: Jul. 3, 2018

(54) MULTIVALENT SIALIC ACID DERIVATIVES

(71) Applicant: Adenovir Pharma AB, Helsingborg (SE)

(72) Inventors: Niklas Arnberg, Umeå (SE); Rémi Caraballo, Holmsund (SE); Mikael Elofsson, Umeå (SE)

(73) Assignee: ADENOVIR PHARMA AB, Helsingborg (SE)

( * ) Notice: Subject to any disclaimer, the term of this patent is extended or adjusted under 35 U.S.C. 154(b) by 17 days.

(21) Appl. No.: 14/914,988

(22) PCT Filed: Aug. 28, 2014

(86) PCT No.: PCT/EP2014/068252
§ 371 (c)(1),
(2) Date: Feb. 26, 2016

(87) PCT Pub. No.: WO2015/028548
PCT Pub. Date: Mar. 5, 2015

(65) Prior Publication Data
US 2016/0207955 A1 Jul. 21, 2016

(30) Foreign Application Priority Data
Aug. 28, 2013 (SE) ..................................... 1350991

(51) Int. Cl.
*C07H 15/26* (2006.01)
*A61K 9/08* (2006.01)
*A61K 9/48* (2006.01)

(52) U.S. Cl.
CPC .............. *C07H 15/26* (2013.01); *A61K 9/08* (2013.01); *A61K 9/48* (2013.01)

(58) Field of Classification Search
CPC ............. C07H 15/26; A61K 9/48; A61K 9/08
USPC ........................................................ 514/25
See application file for complete search history.

(56) References Cited

FOREIGN PATENT DOCUMENTS

| KR | 20110131029 A | 6/2013 |
|---|---|---|
| WO | 200137846 A1 | 5/2001 |
| WO | 2007011696 A2 | 1/2007 |
| WO | 2011003876 A1 | 1/2011 |
| WO | 2011158068 A1 | 12/2011 |
| WO | 2011158200 A1 | 12/2011 |

OTHER PUBLICATIONS

PCT International Search Report and Written Opinion for Application No. PCT/EP2014/068252, dated Oct. 7, 2014.
Alberto Marra et al., "Synthesis of sialoclusters appended to calix[4]arene platforms via multiple azide-alkyne cycloaddition. New inhibitors of hemagglutination and cytopathic effect mediated by BK and influenza A viruses," Organic & Biomolecular Chemistry, Royal Society of Chemistry, GB, vol. 6, No. 8, Apr. 21, 2008, pp. 1396-1409.
Ilona Papp et al., "Inhibition of Influenza Virus Activity by Multivalent Glycoarchitectures with Matched Sizes," Chembiochem, vol. 12, No. 6, Apr. 11, 2011, pp. 887-895.
Lisa Moni et al., "Immobilization ofcalix[4]arene-based glycoclusters on TiO2 nanoparticles via click Cu(i)-catalyzed azide-alkyne coupling," Chemical Communications, vol. 46, No. 3, Jan. 1, 2010, p. 475.
Sara Spjut et al., "A Potent Trivalent Sialic Acid Inhibitor of Adenovirus Type 37 Infection of Human Corneal Cells," Angewandte Chemie International Edition, vol. 50, No. 29, Jul. 11, 2011, pp. 6519-6521.
Johansson et al., "Multivalent sialic acid conjugates inhibit adenovirus type 37 from binding to and infecting human corneal epithelial cells," Antiviral Research, Elsevier BV, NL, vol. 73, No. 2, Jan. 24, 2007, pp. 92-100.
Johansson et al., "Multivalent HSA Conjugates of 3'-Sialyllactose are Potent Inhibitors of Adenoviral Cell Attachment and Infection," Chembiochem—A European Journal of Chemical Biology, Wiley UCH, Weinheim, DE, vol. 6, No. 2, Feb. 4, 2005, pp. 358-364.
Aplander et al., "Molecular Wipes: Application to Epidemic Keratoconjuctivitis", Journal of Medicinal Chemistry, ACS Publications, SE, 2011, vol. 54, p. 6670.
Johansson et al., "Design, Synthesis, and Evaluation of N-Acyl Modified Sialic Acids as Inhibitors of Adenoviruses Causing Epidemic Keratoconjunctivitis," Journal of Medicinal Chemistry, ACS Publications, SE, 2009, vol. 52, p. 366.
Marra et al., "Steroselective Synthesis of 2-Thioglycosides of N-Acetylneuraminic Acid," Carbohydrate Reset, Elsevier Science PA, NL, 1989, vol. 187, p. 35.
M. Sun et al., "A Unique Aliphatic Tertiary Amine Chromophore: Fluorescence, Polymer Structure, and Application in Cell Imaging," Journal of the American Chemical Society, ACS Publications, P.R. China, 2012, vol. 134(51), p. 20581.
Nilsson et al., "The GD1a glycan is a cellular receptor for adenoviruses causing epidemic keratoconjunctivitis," Nature Medicine, Umea University, SE, 2011, vol. 17, p. 105.
Arnberg et al., "Adenovirus Type 37 Uses Sialic Acid as a Cellular Receptor," Journal of Virology, American Society of Microbiology, SE, 2000, vol. 74, No. 1, p. 42.
Arnberg et al., "Initial Interactions of Subgenus D Adenoviruses with A549 Cellular Receptors: Sialic Acit versus av Integrins," Journal of Virology, American Society of Microbiology, SE, 2000, vol. 74, p. 7691.

*Primary Examiner* — Shaojia Anna Jiang
*Assistant Examiner* — Michael C Henry
(74) *Attorney, Agent, or Firm* — Honigman Miller Schwartz and Cohn LLP

(57) ABSTRACT

Disclosed is tri- or tetravalent sialic acid derivatives comprising a core moiety to which 3 or 4 sialic acid residues are connected via a linker. Such derivatives inhibit the binding of adenovirus to human cells, whereby infections, such as epidemic keratoconjunctivitis, may be treated or prevented by administration of the tri- or tetravalent sialic acid derivatives.

18 Claims, 6 Drawing Sheets

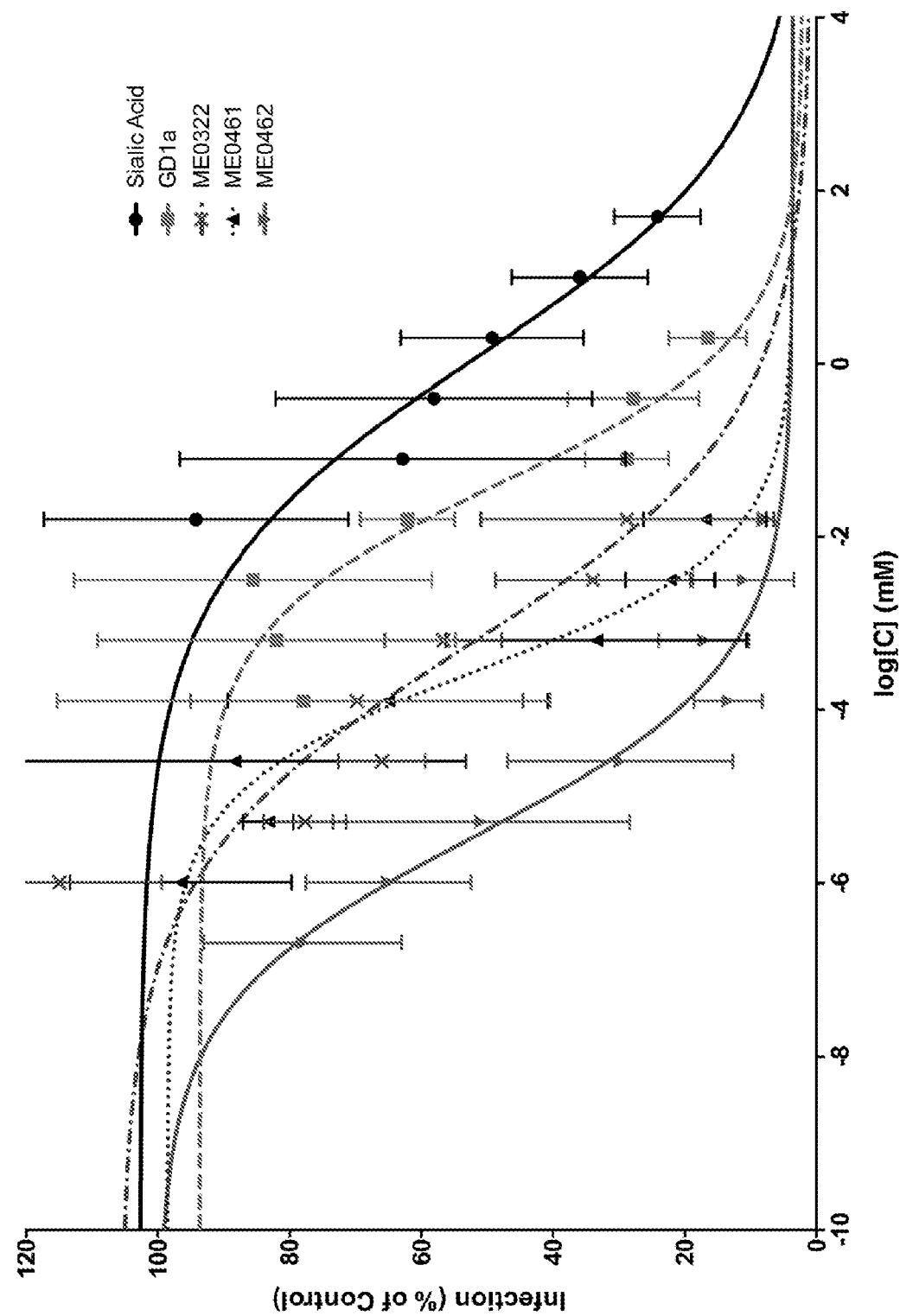

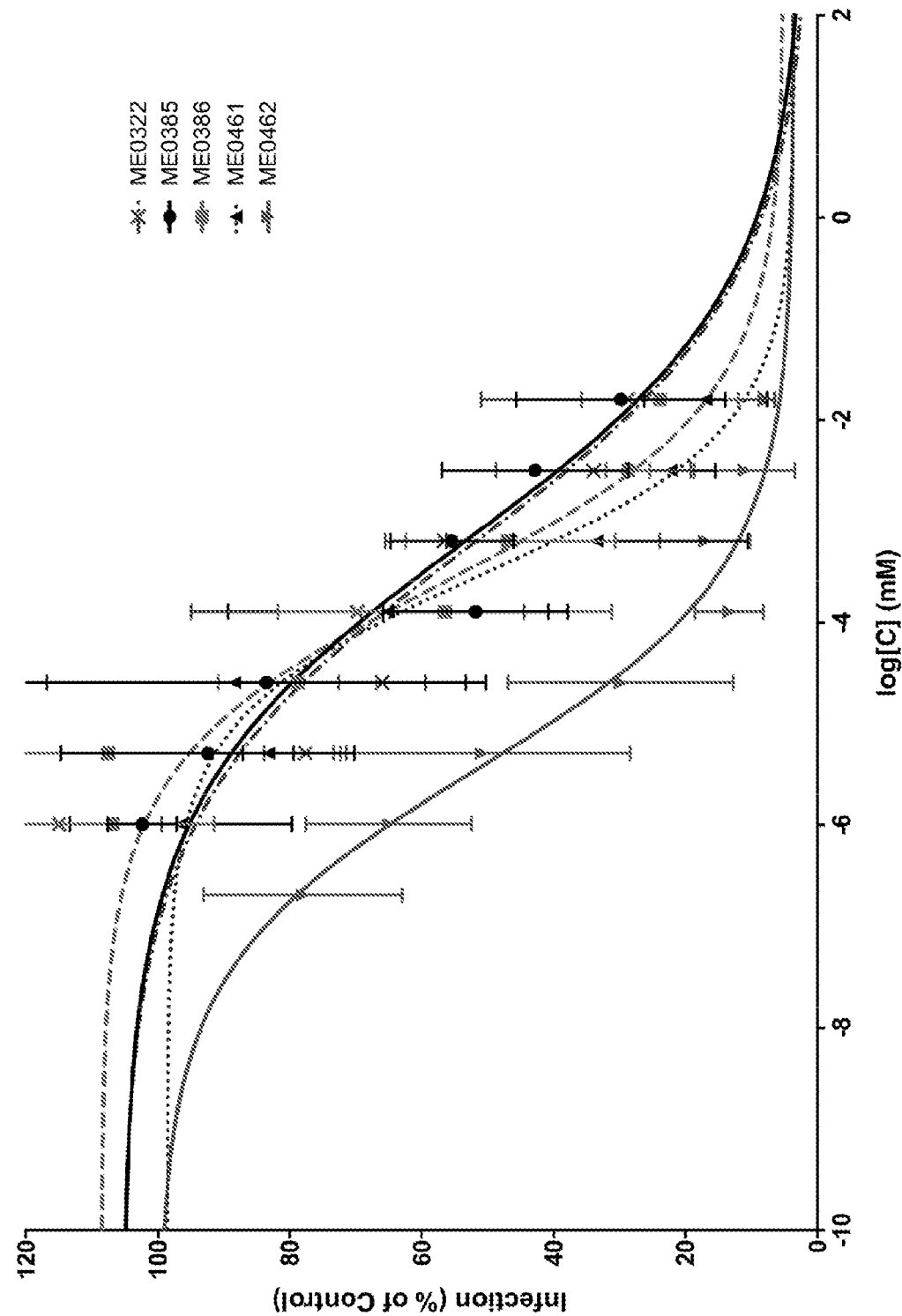

MULTIVALENT SIALIC ACID DERIVATIVES

This application is a 35 USC § 371 United States national stage application of International Application No. PCT/EP2014/068252, filed Aug. 28, 2014, which is incorporated herein by reference in its entirety, and which claims priority to Swedish Patent Application No. 1350991-4, filed Aug. 28, 2013.

FIELD OF THE INVENTION

The present invention relates to novel multivalent sialic acid derivatives, pharmaceutical compositions comprising such derivatives, and a method of treating or preventing epidemic keratoconjunctivitis (EKC) and other ocular diseases caused by virus, which virus binds to terminal sialic residues present on the cell surface, by use of such compounds.

BACKGROUND

Human adenoviruses (HAdV:s), which belong to the mammalian adenovirus genus (*Mastadenovirus*), are commonly encountered infectious agents. In human, adenoviruses are associated with various clinical symptoms including ocular diseases, such as conjunctivitis and epidemic keratoconjunctivitis (EKC).

To date, there are unfortunately no specific antiviral drugs available for the treatment of adenovirus infections. Adenoviruses are obligate intracellular parasites thus indicating that they are fully dependent on the cell's replication machinery. The selective inhibition of adenoviruses replication by antiviral compounds is therefore very difficult to achieve as some of the essential functions of the host cells may also be altered. However, one approach in today's antiviral drug research consists in blocking the cellular receptors of the viruses so that their attachment to and penetration of the cells are precluded. No drug based on such blocking for use in the treatment of epidemic keratoconjunctivitis (EKC) has been registered.

Adenoviruses are ubiquitous in nature and, therefore, new serotypes are still being discovered. Thus, about 60 years after the isolation of the first HAdV:s, over 50 new serotypes that are grouped into seven species (A-G) have been identified.

EKC is a severe and highly contagious ocular infection that is contracted by millions of individuals each year. Among the adenovirus serotypes responsible for EKC, HAdV-8, HAdV-19 and HAdV-37 remain the principal causative agents of the infection, but recently also HAdV-53, HAdV-54 and HAdV-56 have emerged as novel EKC-causing types. Associated symptoms are keratitis, conjunctivitis, edema, pain, lacrimation, formation of pseudomembranes and decreased vision. Because these viruses are spread by contact (e.g. hand to eye contact), EKC is frequent in densely populated areas and in medical wards with insufficient hygiene precautions. The infection commonly last for up to two weeks; however, some patients continue to suffer from sight impairment for several months, years or even permanently.

The viral life cycle is initiated by the binding of adenoviruses, via their homotrimeric fiber knobs, to sialic acid-containing glycans that are situated on epithelial cells in the cornea and/or conjunctiva. The fiber knobs, located at the most distal part of each of the 12 fibers that are protruding from the adenovirus virion, hold the carbohydrate recognition domains. Lately, glycoproteins with glycans corresponding to the glycans in the GD1a gangliosides were evidenced as functional receptors for the infection of ocular cells by EKC-causing adenoviruses. The crystal structure of the HAdV-37-GD1a complex showed that the terminal sialic acid residues located on each of the two branches of the GD1a glycan were accommodated into two out of three carbohydrate recognition sites on top of the HAdV-37 fiber knob.

Thus, inhibition of adenoviruses with natural or synthetic sialic acid derivatives may prevent the virion to attach to, penetrate into and infect new cells (cf. WO 01/037846 among others). As a result, the infection would become limited. Importantly and especially in the case of EKC, the poor pharmacologic properties of carbohydrate-based drugs that include rapid serum clearance and poor cellular uptake can be bypassed by the use of a topical mode of administration (e.g. cream, ointment, eye drops).

WO 01/037846 discloses that adenoviral infections and in particular ocular adenoviral infections, e.g. kerato-conjunctivitis, may be treated or alleviated by the administration of a substance, interfering with the interaction between the virus and the sialic acid receptor, such as sialic acid, in a therapeutically effective amount. Unfortunately the weak interactions between carbohydrates and proteins limit the use of carbohydrates as drugs.

Attempts to overcome said limitations have been made by using a glycoconjugate with several sialic acid derivatives linked to human serum albumin (SA-HSA). However, such polyvalent glycoconjugates are for several reasons not suitable as pharmaceuticals. The exact structure and composition of SA-HSA will vary between different molecules. Accordingly, SA-HSA represents a type of structure, which is hard to structurally define. Furthermore, the composition of the SA-HSA derivatives will vary between different batches even if produced in the same manner. From a safety and a regulatory perspective this is a significant drawback. In addition the use of a protein, i.e. HSA, which is derived from human plasma, is a major disadvantage. The origin of HSA makes it hard to produce larger amounts of a pharmaceutical based on HSA. Furthermore, contamination by infectious agents, such as viruses or prions, may not be excluded in HSA derived from human plasma. Accordingly, a product based on HSA, is not suitable as a pharmaceutical product, and a polyvalent alternative would be highly desirable.

In WO 2011/003876 novel amphiphilic sialic acid derivatives forming multivalent aggregates in aqueous solutions are disclosed. The aggregates are disclosed to overcome the drawbacks associated with SA-HSA, thereby being by useful in treating EKC. Further aspects of such derivatives have been disclosed by Aplander et al in *J. Med. Chem.* 2011, 54, 6670.

Further, covalently bound multivalent efficient sialic acid-based inhibitors of HAdV-37 infection of human corneal epithelial (HCE) cells have been reported in the art (cf. Spjut et al. *Angew. Chem. Int. Ed.* 2011, 50, 6519; Johansson et al. *Chembiochem* 2005, 6, 358; and Johansson et al *Antivir. Res.* 2007, 73, 92). In order to circumvent the relatively low efficacy of monovalent sialic acid derivatives, the authors took advantage of the trimeric binding site at the HAdV-37 fiber knob. The use of tri- and tetravalent sialic acid derivatives that can simultaneously bind to more than one carbohydrate recognition domain per knob, as disclosed by Spjut et al, considerably improved the inhibitory potency in comparison to monovalent sialic acid compounds.

For instance, a compound denoted ME0322, being a synthetic trivalent sialic acid derivative wherein squaric acid is used to link sialic acid to a central core unit, was reported with four orders of magnitude more potent than the natural sialic acid monosaccharide. Further, ME0322 was as effective as 17-valent sialic acid-HSA conjugate in preventing binding of the virus to the fiber knob. Interestingly, ME0322 was found to be far more potent than the HSA-conjugate in inhibiting infection of human corneal epithelial (HCE) cells by HAdV-37.

While said compound indeed shows interesting properties, it would still be useful to provide a multivalent sialic acid derivative having even further improved potency in terms of preventing the attachment of HAdV-37 virions to human corneal epithelial (HCE) cells.

Thus, there is a still a need in the art for a low molecular, multivalent sialic acid derivative displaying high efficacy in preventing the attachment of HAdV-37 virions to human corneal epithelial (HCE) cells. Such a derivative would be useful in treating and preventing EKC.

SUMMARY

Consequently, the present invention seeks to mitigate, alleviate, eliminate or circumvent one or more of the above-identified deficiencies in the art and disadvantages singly or in any combination by providing a tri- or tetravalent sialic acid derivate, said derivative comprising a core moiety to which 3 or 4 groups according to formula A or B are attached (A)

(B)

wherein

"X" is O (oxygen), NH or S (sulfur);

R1 is C1-3 alkyl, phenyl, OC1-2 alkyl, CF3, or NHC1-2 alkyl;

the integer "n1" is 2 to 8;

the integer "n2" is 1 to 8; and the waved line indicates the point of attachment to the core moiety;

as a free base, an acid in its non-charged protonated form, a zwitterion, a pharmaceutically acceptable addition salt, solvate, or solvate of a salt thereof.

According to aspects of the invention:

"X" may be O (oxygen); R1 may be methyl, the integer "n1" may be 2 to 3; said groups may be groups according to formula A; and/or the molecular weight of said derivate in its free form is 1,500 Da or less; or "X" may be O (oxygen); R1 may be methyl, the integer "n2" may be 1, 2 or 3; said groups may be groups according to formula B; and/or the molecular weight of said derivate in its free form is 1,500 Da or less.

Further, said core moiety may be a moiety according any one of the formulae I to V (I)

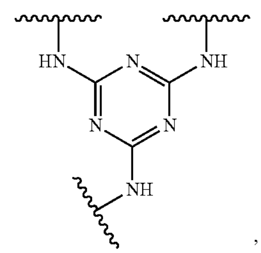

, (II)

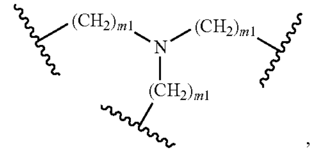

, (III)

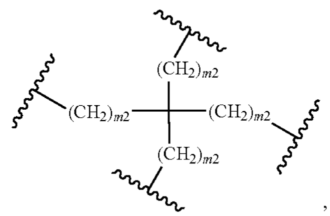

, (IV)

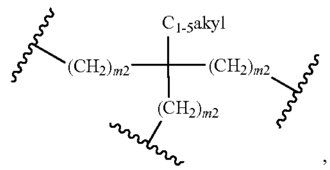

, and (V)

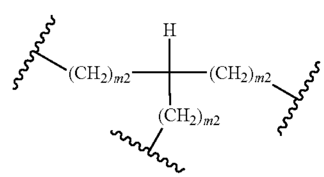

wherein the groups attached to the moiety I, are groups according to Formula A;

the integer "m1" in Formula II is 1 to 8, if the groups to the moiety II are groups according to Formula A;

the integer "m1" in Formula II is 2 to 8, if the groups attached to the moiety II are groups according to Formula B;

the integer "m2" is 1 to 8; and the waved lines indicate the point of attachment to the groups according to formula A or B.

According to another aspect, there is provided a pharmaceutical composition for administration to the eye comprising sialic acid derivate of the herein above described type and at least one pharmaceutical acceptable excipient. The pharmaceutical composition may be an aqueous composition comprising 0.001 to 10 mM, such as 0.01 to 1 mM, of a sialic acid derivate. The water content is such an aqueous composition may be at least 90 wt %. Further such an aqueous composition may comprise an agent, such as glycerol, to provide an isotonic solution.

According to another aspect, the herein above described sialic acid derivate or pharmaceutical composition comprising such a derivative, are for use in therapy.

According to another aspect, the herein above described sialic acid derivate or pharmaceutical composition comprising such a derivative, are for use in the treatment and/or prevention of an ocular infection caused by a virus, which binds to terminal sialic residues present on the cell surface of the cell to be infected by said virus. The infection may be an infection caused by a virus selected from the group consisting of HAdV-8, HAdV-19, HAdV-37, HAdV-53, HAdV-54, and HAdV-56. Further may the infection be epidemic keratoconjunctivitis.

Further, advantageous features of various embodiments of the invention are defined in the dependent claims and within the detailed description below.

DETAILED DESCRIPTION OF PREFERRED EMBODIMENTS

As used herein, the term "addition salt" is intended to mean salts formed by the addition of a pharmaceutical acceptable acid, such as organic or inorganic acids, or a pharmaceutical acceptable base. The organic acid may be, but is not limited to, acetic, propanoic, methanesulfonic, benzenesulfonic, lactic, malic, citric, tartaric, succinic or maleic acid. The inorganic acid may be, but is not limited to, hydrochloric, hydrobromic, sulfuric, nitric acid or phosphoric acid. The base may be, but is not limited to, ammonia and hydroxides of alkali or alkaline earth metals. The term "addition salt" also comprises the hydrates and solvent addition forms, such as hydrates and alcoholates.

As used herein, "alkyl" used alone or as a suffix or prefix, is intended to include both branched and straight chain saturated aliphatic hydrocarbon groups having a specified number of carbon atoms. For example "C1-6 alkyl" denotes alkyl having 1, 2, 3, 4, 5 or 6 carbon atoms.

Compounds

The trivalent sialic acid derivate denoted ME0322 (see below), known in the art to inhibit binding of HAdV-37 human corneal epithelial cells, has three main elements, a core moiety, sialic acid residues, and linkers, connecting the core moiety and the sialic acid residues. In the linker, a coupling residue based on squaric acid is present. The trivalent sialic acid derivative ME0322 was designed in a manner to provide for sufficient flexibility as to allow for interaction with all three sialic acid binding sites of the fiber knob simultaneously. Seemingly, a resolved crystal structure of a complex of HAdV-37 fiber head and ME0322 confirms that the compound indeed is able to bind to all three sialic acid binding sites simultaneously, thereby confirming that the flexibility provided by the linkers is sufficient.

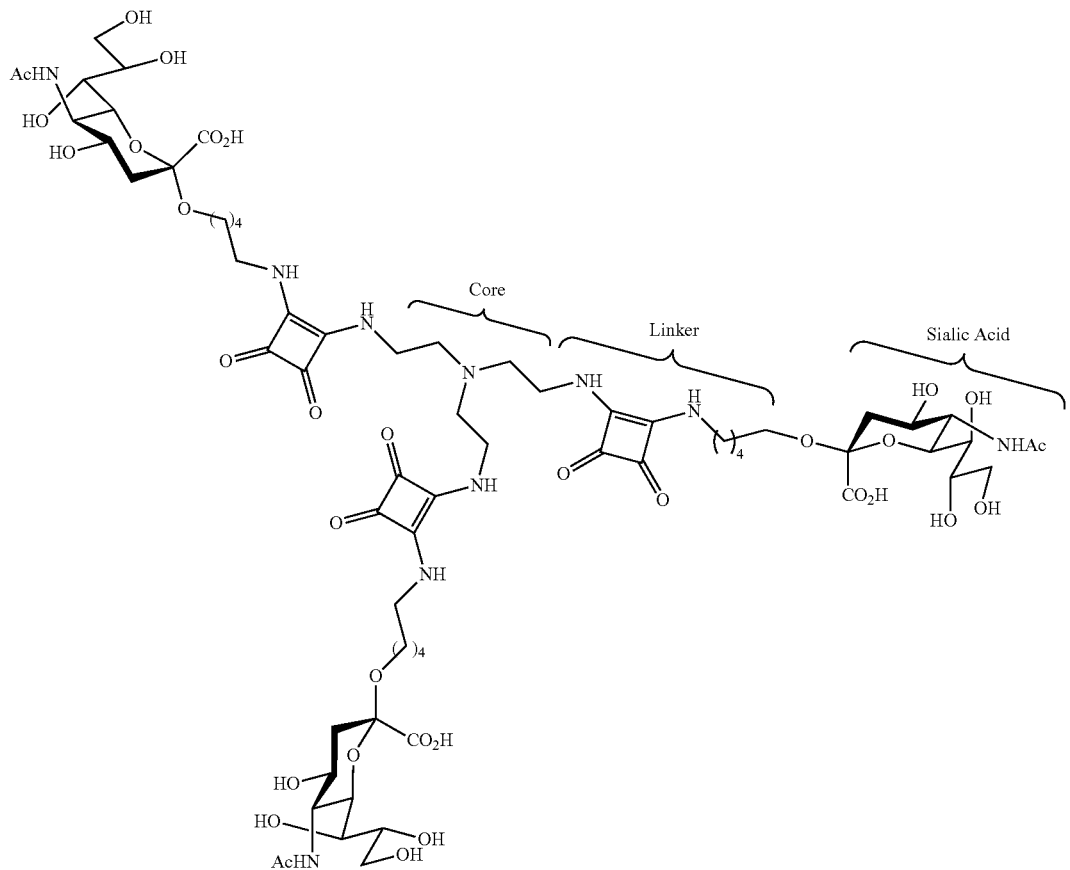

ME0322

It was speculated that replacing the squaric acid residue with another coupling residue, providing means for establishing additional contacts with the carbohydrate recognition sites at the HAdV-37 fiber knob, would potentially increase the binding affinity even further. Surprisingly, the present inventors have also confirmed that replacing the squaric acid coupling residue, as present in ME0322, with a triazole acid coupling residue indeed results in multivalent sialic acid derivatives with increased potency for preventing binding of HAdV-37 to human corneal epithelial cells.

Thus, an embodiment relates to a tri- or tetravalent sialic acid derivate, said derivative comprising a core moiety to which 3 or 4 groups according to formula A or B are attached (A)

(B)

wherein

"X" is O (oxygen), NH or S (sulfur);

R1 is C1-3 alkyl, phenyl, OC1-2 alkyl, CF3, or NHC1-2 alkyl;

the integer "n1" is 2 to 8;

the integer "n2" is 1 to 8; and the waved line indicated the point of attachment to the core moiety.

Such compounds may be present as free bases, as acids in their non-charged protonated form, as pharmaceutically acceptable addition salts, as solvates, or as solvates of a pharmaceutically acceptable addition salt. As the compounds comprise an alkaline triazole residue as well as an acidic carboxylic moiety, they may also be present as zwitterions. Further, said compound may be present as a pure stereoisomer, or in a racemic, diastereomeric, scalemic or anomeric mixture comprising said compound. Preferably, said compound is present as a pure stereoisomer, or as an anomeric mixture.

If present in an anomeric mixture, it is preferred if the α-anomer prevails. Accordingly, its is preferred if 75% or more, such as more than 90%, 95%, 99% or even more than 99.9% of a compound is present as the α-anomer. The corresponding β-anomers are depicted below.

While, also N- and S-glycosides are of interest, O-glycosides are preferred. Thus, "X" in Formula A and B are "O" (oxygen) according to an embodiment.

For previous HSA derivatives being somewhat related to the present one, it has previously be shown (Johansson et al. *J. Med. Chem.* 2009, 52, 366) that R1 not is restricted to methyl in compounds having affinity for the carbohydrate recognition sites of the HAdV-37 fiber knob. However, while R1 in tri- or tetravalent sialic acid derivate disclosed herein not is restricted to methyl, it is preferred if R1 is methyl.

In tri- or tetravalent sialic acid derivate disclosed herein the sialic acid residue is attached to the triazole residue via an alkylene. While an alkylene is preferred, one could also envisage replacing the alkylene with let say a short PEG-linker or a linker comprising a cycloalkyl moiety, such as cyclopropyl. The alkylene may be of various lengths, i.e. ethylene to octylene for tri- or tetravalent sialic acid derivate comprising groups according to formula A and methylene to octylene for tri- or tetravalent sialic acid derivate comprising groups according to formula B. However, it is preferred if the alkylene is ethylene or propylene. Thus, it is preferred if the integer "n1" is 2 or 3 in tri- or tetravalent sialic acid derivate comprising groups according to formula A. Similarly, it is preferred if the integer "n2" is 1, 2 or 3 in tri- or tetravalent sialic acid derivate comprising groups according to formula B.

Tri- or tetravalent sialic acid derivate as disclosed herein may be obtained by coupling of sialic acid residue comprising azide group with a core moiety comprising ethyne groups in a cupper (I) catalyzed azide-alkyne Huisgen cycloaddition (cf. experimental details further below). Similarly, a sialic acid residue comprising ethyne group may be coupled with a core moiety comprising azide groups in the presence of cupper (I). According to an embodiment, tri- or tetravalent sialic acid derivatives as disclosed herein comprise groups according to formula A. According to another embodiment, tri- or tetravalent sialic acid derivatives as disclosed herein comprise groups according to formula B. Seemingly, compounds comprise groups according to formula B may be somewhat more potent than compounds comprising groups according to formula A, at least with certain linker lengths.

Although tripropargylamine and tris (2-azidoethyl)amine, respectively were found to be useful as core moieties in obtaining tri- or tetravalent sialic acid derivate with increased affinity for the carbohydrate recognition sites at the HAdV-37 fiber knob, the present invention is by no means limited to only this type of trivalent core moiety. Other small molecular, structurally well defined compounds comprising three or four ethyne, or azide, groups may also be coupled with sialic acid residues in the presence of cupper (I) to obtain tri- or tetravalent sialic acid derivates.

According to an embodiment, the molecular weight of the tri- or tetravalent sialic acid derivate in its free form is 2,500 Da or less, such as 2,000 or less, or 1,500 Da or less. As the three sialic acid binding sites of the fiber knob is located fairly close (i.e. approx. 10 Å) to each other, it is preferred if the sialic acid residues of the tri- or tetravalent sialic acid derivate not are too spaced apart. Further, a too flexible core moiety or too large distance between the sialic acid residues may affect the binding of the derivative to the fiber knob negatively. A small and more rigid derivative will also result in less entropy losses when binding the fiber knob protein and thus contribute to improved potency.

As already explained the core moiety may of various types. According to an embodiment the core moiety is a moiety according any one of the formulae I to V (I)

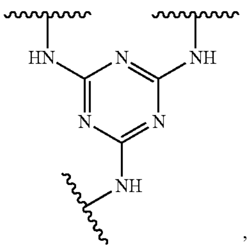

, (II)

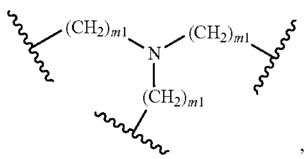

, (III)

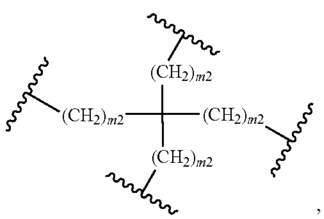

, (IV)

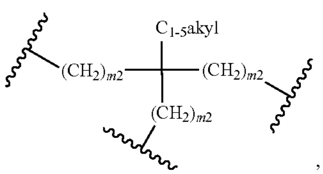

,

-continued (V)

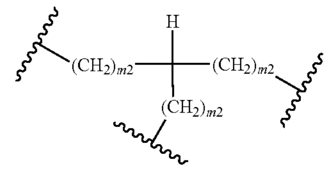

wherein the groups according to formula A or B attached to the moiety I, are groups according to Formula A;

the integer "m1" in Formula II is 1 to 8, if the groups according to formula A or B attached to the moiety II are groups according to Formula A;

the integer "m1" in Formula II is 2 to 8, if the groups according to formula A or B attached to the moiety II are groups according to Formula B;

the integer "m2" is 1 to 8; and the waved lines indicate the point of attachment to the groups according to formula A or B.

While the exact nature of the core moiety is of less importance for the binding affinity, it anyhow has been found that it is preferred if the core moiety is a moiety according to formula II. Furthermore, preferably the integer "m1" is 1 to 3 and the integer "m2" is 1 to 3. Further, the groups according to formula A or B attached to the moiety II are according to an embodiment groups according to Formula A. According to another embodiment they are groups according to Formula B.

According to one embodiment, a tri- or tetravalent sialic acid derivate as disclosed herein comprises groups according to Formula A and is selected from the group consisting of:

Tris ((1-(2-O-(5-N-acetamido-3,5-dideoxy-D-glycero-α-D-galacto-2-nonulopyranosylonic acid))-2-oxoethyl-1H-1,2,3-triazol-4-yl)methyl)amine;

Tris ((1-(2-O-(5-N-acetamido-3,5-dideoxy-D-glycero-α-D-galacto-2-nonulopyranosylonic acid))-3-oxopropyl-1H-1,2,3-triazol-4-yl)methyl)amine;

Tris ((1-(2-O-(5-N-propanoylamido-3,5-dideoxy-D-glycero-α-D-galacto-2-nonulopyranosylonic acid))-2-oxoethyl-1H-1,2,3-triazol-4-yl)methyl)amine; and Tris ((1-(2-O-(5-N-propanoylamido-3,5-dideoxy-D-glycero-α-D-galacto-2-nonulopyranosylonic acid))-3-oxopropyl-1H-1,2,3-triazol-4-yl)methyl)amine According to such an embodiment, it is preferred if the tri- or tetravalent sialic acid derivate is Tris ((1-(2-O-(5-N-acetamido-3,5-dideoxy-D-glycero-α-D-galacto-2-nonulopyranosylonic acid))-3-oxopropyl-1H-1,2,3-triazol-4-yl)methyl)amine, i.e.

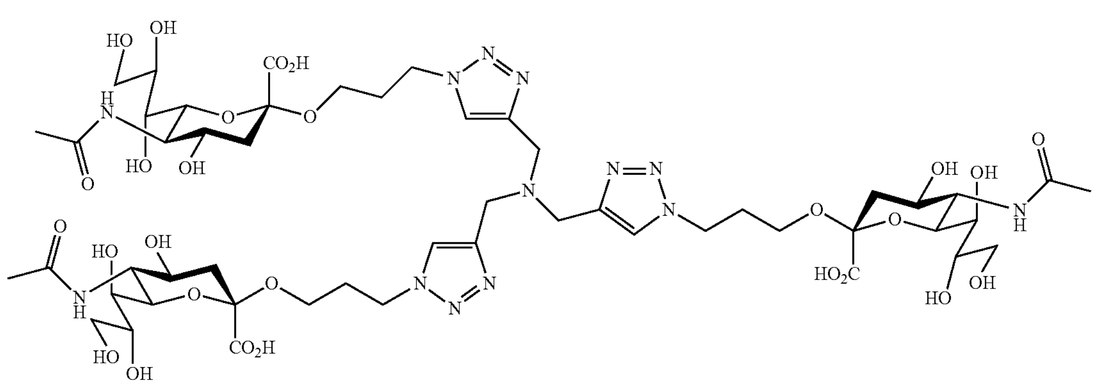

According to another embodiment, the tri- or tetravalent sialic acid derivate as disclosed herein comprises groups according to Formula B and is selected from the group consisting of:

Tris ((4-(2-O-(5-N-acetamido-3,5-dideoxy-D-glycero-α-D-galacto-2-nonulopyranosylonic acid))-2-oxomethyl-1H-1,2,3-triazol-1-yl)ethyl)amine;

Tris ((4-(2-O-(5-N-propanoylamido-3,5-dideoxy-D-glycero-α-D-galacto-2-nonulopyranosylonic acid))-2-oxomethyl-1H-1,2,3-triazol-1-yl)ethyl)amine;

Tris ((4-(2-O-(5-N-acetamido-3,5-dideoxy-D-glycero-α-D-galacto-2-nonulopyranosylonic acid))-2-oxoethyl-1H-1,2,3-triazol-1-yl)ethyl)amine; and Tris ((4-(2-O-(5-N-propanoylamido-3,5-dideoxy-D-glycero-α-D-galacto-2-nonulopyranosylonic acid))-2-oxoethyl-1H-1,2,3-triazol-1-yl)ethyl)amine.

According to such an embodiment, it is preferred if the tri- or tetravalent sialic acid derivate is Tris ((4-(2-O-(5-N-acetamido-3,5-dideoxy-D-glycero-α-D-galacto-2-nonulopyranosylonic acid))-2-oxomethyl-1H-1,2,3-triazol-1-yl)ethyl)amine, i.e.

does not cause any unwanted effects in the subjects to whom it is administered. Such pharmaceutically acceptable excipients are well-known in the art.

According to one embodiment, such a pharmaceutical composition as disclosed herein is a pharmaceutical composition suitable for administered to the eye. Without limitation typical examples of pharmaceutical compositions suitable for administration to the eye comprise eye drops, ointments, sprays, dressings, and gels.

A pharmaceutical composition suitable for administration to the eye may be an aqueous composition. Such an aqueous composition may have a water content of 90 wt % water or more, such as 90 to 99.9, 95 to 99, or 95 to 98 wt % water. Further, an aqueous composition comprising a tri- or tetravalent sialic acid derivate as disclosed herein, may comprise 0.001 to 10 mM, such as 0.01 to 1 mM, of the tri- or tetravalent sialic acid derivate.

Furthermore an aqueous composition may comprise an agent to provide an isotonic solution. Accordingly, an aqueous composition may comprise an agent selected from the group consisting of sodium chloride, glycerol, polyethyl-

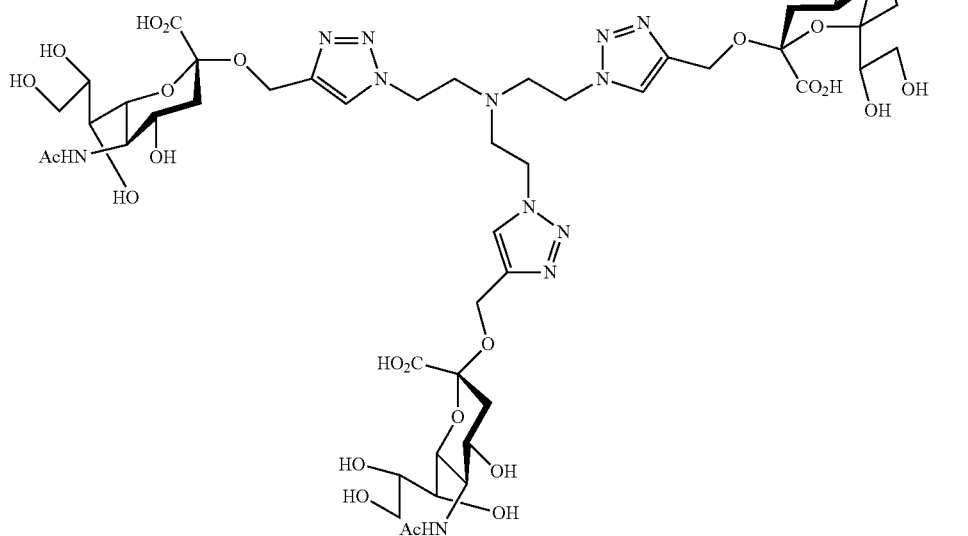

Pharmaceutical Composition

Another embodiment of the invention relates to a pharmaceutical composition, e.g. a medicament for treatment and/or prevention of EKC, comprising a tri- or tetravalent sialic acid derivate as disclosed herein. Such a pharmaceutical composition may further comprise pharmaceutically acceptable excipients, such as carriers, diluents, and/or stabilizers. Depending on the applicable regulation, the pharmaceutical composition may either be classified as a pharmaceutical, or as a medical device, for treatment or prevention of an infection in the eye. The mere fact that the composition is referred to as a pharmaceutical composition herein should not be interpreted as excluding the registration of the composition as a medical device. The virus binding properties of the tri- or tetravalent sialic acid derivate implies that it may be also be used for example to prevent contamination of contact lenses, such as in the form of a lens solution.

In this context "Pharmaceutically acceptable" means an excipient that, at the dosage and concentration employed, eneglycol, saccharides, such as monosaccharides, e.g. glucose and mannitol, and disaccharides, e.g. sucrose.

According to one embodiment a pharmaceutical composition as disclosed herein is an aqueous composition comprising an electrolyte, such as sodium chloride. Preferably the content of the electrolyte should be close to the iso-osmotic concentration, such as about 0.9 wt % for sodium chloride.

According to another embodiment a pharmaceutical composition as disclosed herein is an aqueous composition comprising glycerol. The content of glycerol may be 2 to 3 wt %, such as 2.3 to 2.3 or 2.5 to 2.7 wt %. Preferably said content should be close to the iso-osmotic concentration, such as about 2.6 wt %.

Further, it may be of interest to adjusting the pH of the pharmaceutical composition in order to provide a composition having a pH close the physiological one. Thus, the pharmaceutical composition according to one embodiment is an aqueous pharmaceutical composition having a pH of about 6.5 to 8. Preferably, said pH is closer to physiological pH, such as about 7.2 to 7.8.

As the tri- or tetravalent sialic acid derivates disclosed herein comprise acidic carboxylic acid moieties as well as alkaline moieties, including triazole moieties, the pharmaceutical composition may comprise a pharmaceutical acceptable acid and/or base to adjust the pH to the desired level. Also, the pharmaceutical composition may be buffered. A buffered pharmaceutical composition typically comprises buffering species, such as $HCO_3^-/CO_3^{2-}$ or $H_2PO_47$ $HPO_4^{2-}$. Further, the buffered pharmaceutical composition may be borate buffered.

According to another embodiment, the pH of the pharmaceutical composition is slightly lower than physiological, such as about 5 to 7. A composition with an acidic pH, i.e. below 7, has the advantage of being less susceptible to the growth of microorganisms. Further, growth of microorganisms may be prevented by adding a preservative to the pharmaceutical composition. According to one embodiment a pharmaceutical composition as disclosed herein does thus comprise a preservative. Examples of such preservatives benzalkonium chloride, benzoic acid, butylated hydroxyanisol, parabens, such as butyl paraben, propyl paraben, ethyl paraben, methyl paraben and mixtures thereof, phenoxyethanol, phenylethyl alcohol or sorbic acid. A pharmaceutical composition comprising a preservative may be more suitable for storage. Further, a pharmaceutical composition as disclosed herein may be sterilized, such as by heat sterilization or by sterile filtration.

The pharmaceutical composition as disclosed herein may further also comprise other pharmaceutically acceptable excipients, such as antioxidants, additional isotonicity agents, colouring agents and the like.

In embodiments relating to aqueous pharmaceutical compositions, the composition may comprise suspending and stabilising agents, such as non-ionic surfactants, hydrophilic polymers and the like.

According to one embodiment, a pharmaceutical composition as disclosed herein may comprise a thickening agent. Typically a pharmaceutical composition to be thickened is aqueous. Thickening agents may be employed in order to create a thickened solution, gel, syrup, cream, or ointment. In order to form a thickened solution or gel, a hydrogel-forming material may be employed. Such a hydrogel-forming material may be selected from the group consisting of synthetic polymers, semi-synthetic polymers and natural gums.

Examples of synthetic polymers include polyvinylalcohol, polyvinylpyrrolidone, polyacrylic acid, polyethylene glycol, poloxamer block copolymers. Examples of semi-synthetic polymers include cellulose ethers, such as carboxymethylcellulose, hydroxyethylcellulose, hydroxypropylcellulose, methylcellulose, hydroxypropylmethylcellulose and ethylhydroxyethylcellulose. Examples of natural gums include acacia, alginate, carragenan, chitosan, pectin, starch, xanthan gum.

A thickened solution or gel may be rendered mucoadhesive by employment of materials such as hyaluronic acid and derivatives thereof, cross-linked polyacrylic acids of the carbomer and polycarbophil types, and polymers that readily form gels, which are known to adhere strongly to mucous membranes.

According to one embodiment a pharmaceutical composition as disclosed herein may comprise a block copolymer of the poloxamer type. It is advantageous to use the block copolymer of the poloxamer type, such as polymers comprising polyethylene glycol and polypropylene glycol blocks, as certain poloxamers dispersed in water are thermoreversible. Examples of thermoreversible poloxamers are poloxamer 188 and poloxamer 407.

Thermoreversible poloxamers dispersed in water have a low viscosity but exhibit a marked viscosity increase at elevated temperatures, resulting in a gel formation at body temperature. Thereby the contact time of a pharmaceutical formulation administered to the relatively warm cornea may be prolonged. Accordingly, one embodiment of the invention relates to a pharmaceutical composition, as disclosed herein, which is thermoreversible.

According to one embodiment a pharmaceutical composition as disclosed herein may comprise an additional anti-viral compound. Examples of such compounds include N-chlorotaurin and Povidone-iodine (PVP-I).

N-chlorotaurine (Cl—HN—CH2-CH2-SO3H) is an endogenous antimicrobial agent. It is a mild active chlorine compound produced by granulocytes and monocytes during the oxidative burst. Because of its unspecific reaction mechanism, i.e. oxidation of amino groups, thio and aromatic compounds, it has broad-spectrum microbicidal activity similar to antiseptics. The sodium salt solution of N-chlorotaurine (Cl—HN—CH2-CH2-SO3Na) has been shown to kill in vitro bacteria and fungi. In addition, a virucidal effect has been demonstrated. Povidone-iodine is a stable chemical complex of polyvinylpyrrolidone (povidone, PVP) and elemental iodine.

According to one embodiment a pharmaceutical composition as disclosed herein may comprise an additional anti-viral compound, wherein said anti-viral compound is a compound useful to topically treat infections caused by herpes. Examples of such compounds include the guanosine analogues aciclovir, valaciclovir, penciclovir, and famciclovir, and foscarnet (sodium phosphoneformate hexahydrate).

According to one embodiment a pharmaceutical composition as disclosed herein may comprise a local anesthetic. As EKC may be a very painful disease, it may be advantageous to include a local anesthetic to provide pain relief. Furthermore, such pain relief may have the advantage of encouraging the patient to continue the treatment although the administration it self may be painful. In addition, use of local anesthetic with a rapid onset, may make it possible for the patient to actually open the eye in order to allow further administration of the composition directly to the cornea. Examples of useful local anesthetics include lidocaine, prilocaine, and ropivacaine.

Therapy

According to another embodiment, a tri- or tetravalent sialic acid derivate, or a pharmaceutical composition, as disclosed herein may be used in therapy.

Treatment of Ocular Infections

As already disclosed above, the tri- or tetravalent sialic acid derivates, as disclosed herein, were found to inhibit the binding of HAdV-37 to human corneal cells.

Accordingly, one embodiment of the invention relates a tri- or tetravalent sialic acid derivate or a pharmaceutical composition, as disclosed herein, for use in the treatment and/or prevention of an ocular infection caused by a virus, which virus binds to terminal sialic residues present on the cell surface of the cell to be infected by said virus.

Similarly, one embodiment of the invention relates to use of a tri- or tetravalent sialic acid derivate or a pharmaceutical composition, as disclosed herein, for the manufacture of a medicament for use in the treatment and/or prevention of an ocular infection caused by a virus, which virus binds to terminal sialic acid residues present on the cell surface of the cell to be infected by said virus.

Yet another embodiment relates to a method of prevention and/or treatment of an ocular infection caused by a virus, which virus binds to terminal sialic acid residues present on the cell surface of the cell to be infected by said virus, such as EKC, comprising administering to a mammal, including man, in need of such prevention and/or treatment, a therapeutically effective amount of a tri- or tetravalent sialic acid derivate as disclosed herein or a pharmaceutical composition comprising a therapeutically effective amount of a tri- or tetravalent sialic acid derivate as disclosed herein. Preferably, said tri- or tetravalent sialic acid derivate or pharmaceutical composition is administered to the eye in such a method.

Example of viruses binding to terminal sialic acid residues present on the cell surface and thereby allowing for infection of said cells to cause infections, such as ocular infections, include HAdV-8, HAdV-19, HAdV-37, HAdV-53, HAdV-54 and HAdV-56. Examples of adenoviruses causing ocular infections by binding to terminal sialic acid residues present on the cell surface include HAdV-8, HAdV-19 and HAdV-37, a typical example being HAdV-37.

According to one embodiment the ocular infection to be treated and/or prevented by use of the present tri- or tetravalent sialic acid derivate or composition is epidemic keratoconjunctivitis (EKC).

A pharmaceutical composition according to embodiments herein may be administered to a patient in a pharmaceutically effective dose. By "pharmaceutically effective dose" is meant a dose that is sufficient to produce the desired effects in relation to the condition for which it is administered. The exact dose may be dependent on the activity of the tri- or tetravalent sialic acid derivate, manner of administration, nature and severity of the disorder and/or disease and the general conditions, such as age and body weight of the patient.

According to one embodiment, a pharmaceutical composition as disclosed herein is to be administered one or several times per day. Typically, such a pharmaceutical composition will be administered three times a day, although other dose regimen may be used as well.

When used herein, "prevent/preventing" should not be construed to mean that a condition and/or a disease never might occur again after use of a compound or pharmaceutical composition according to embodiments disclosed herein to achieve prevention. Further, the term should neither be construed to mean that a condition not might occur, at least to some extent, after such use to prevent said condition. Rather, "prevent/preventing" is intended to mean that the condition to be prevented, if occurring despite such use, will be less severe than without such use.

According to one embodiment treatment does also encompass pre-treatment, i.e. prophylactic treatment.

General Remarks

Although the present invention has been described above with reference to specific illustrative embodiments, it is not intended to be limited to the specific form set forth herein. Any combination of the above mentioned embodiments should be appreciated as being within the scope of the invention. Rather, the invention is limited only by the accompanying claims and other embodiments than the specific above are equally possible within the scope of these appended claims.

In the claims, the term "comprises/comprising" does not exclude the presence of other species or steps. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc. do not preclude a plurality. The phrases "at least one" or "one or more" refer to 1 or a number greater than 1, such as to 1, 2, 3, 4, 5, 6, 7, 8, 9, or 10.

Experimental

The following examples are mere examples and should by no mean be interpreted to limit the scope of the invention. Rather, the invention is limited only by the accompanying claims.

BRIEF DESCRIPTION OF THE DRAWINGS

FIGS. 1b, 3a and 3b: Effect of the set of trivalent sialic acid derivatives on HAdV-37 binding to and infection of HCE cells—Infection at different concentrations of the inhibitors (data are presented as % of control that is the value obtained in the absence of inhibitor).

Figure 1A:
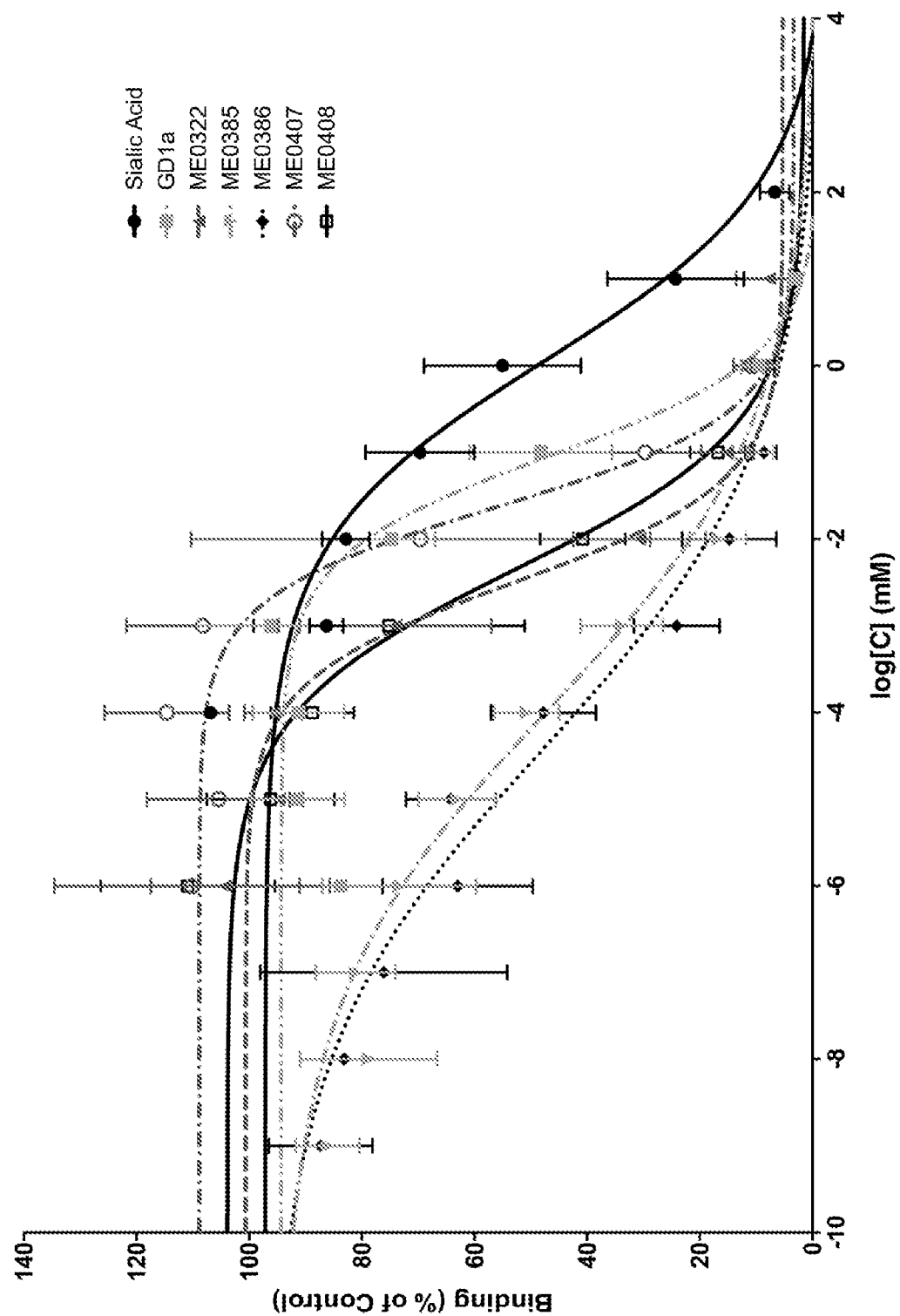
FIGS. 1a, 2a and 2b: Effect of the set of trivalent sialic acid derivatives on HAdV-37 binding to and infection of HCE cells—Virion binding in the presence of inhibitors at different concentrations (data are presented as % of control that is the value obtained in the absence of inhibitor).

GENERAL CHEMICAL PROCEDURES $^1$H NMR and $^{13}$C NMR spectra were recorded with a Bruker DRX-400 spectrometer at 400 MHz and 100 MHz respectively. NMR experiments were conducted at 298 K in $CDCl_3$ (residual solvent peak=7.26 ppm ($\delta$H)), $CD_3OD$ (residual solvent peak=3.31 ppm ($\delta$H) and 49.00 ppm ($\delta$C)) and $D_2O$ (residual solvent peak=4.79 ppm ($\delta$H)).

LCMS was carried out with a Waters LC system equipped with an Xterra C18 column (50×19 mm, 5 μm, 125 Å), eluted with a linear gradient of $CH_3CN$ in water, both of which contained formic acid (0.2%). A flow rate of 1.5 mL/min was used and detection was performed at 214 nm. Mass spectra were obtained on a Water micromass ZQ 2000 using positive and negative electrospray ionization.

Semi-preparative HPLC separations were performed on a Gilson system HPLC, using a Nucleodur C-18 column HTEC 5 μm (VP 250/21) with a flow rate 20 mL/min, detection at 214 nm and eluent system: A. aq. 0.005% $CF_3COOH$, and B. 0.005% $CF_3COOH$ in $CH_3CN$.

Column chromatography was performed on silica gel (Merck, 60 Å, 70-230 mesh ASTM). Thin Layer Chromatography (TLC) were performed on Silica gel 60 $F_{254}$ (Merck) with detection under UV light and/or development with 5% $H_2SO_4$ in EtOH and heat.

Optical rotations were measured with a Perkin-Elmer 343 polarimeter at 20° C. Organic solvents were dried using a Glass Contour Solvent Systems (SG Water USA) except $CH_3CN$ and MeOH that were dried over molecular sieves 3 Å.

All commercial reagents were used as received.

The compound denoted ME0322 was synthesized according to published procedure (cf. Spjut et al Angew. Chem. Int. Ed. 2011, 50, 6519). All target compounds were ≥95% pure according to HPLC UV-traces. Statistics were calculated using GraphPad Prism (GraphPad Software, Inc, La Jolla, Calif.).

Synthetic Procedures

General

The compounds of the present invention may be obtained by providing sialic acid with a linker, typically an alkylene linker, having a reactive end-group, i.e. an azide group (cf. the compound depicted to the left below) or ethyne group (cf the compound depicted to the right below).

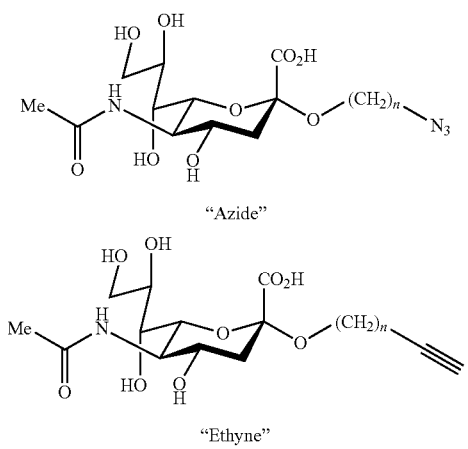

By allowing sialic acid provided with a reactive end-group to react with a core moiety having 3 or 4 reactive groups, i.e. azide or ethyne moieties, in an azide-alkyne Huisgen cycloaddition, typically in the presence of cupper (I) acting as catalyst, compounds of the present invention may be obtained. As readily recognized by the skilled person it may be advantageous, or even necessary, to protect various groups at various stage of the synthesis. The skilled person is familiar with what groups to be used.

Example 1

Use of Tripropargylamine as Core Moiety

The route to unmodified N-Acyl trivalent sialic acids, such as Tris ((1-(2-O-(5-N-acetamido-3,5-dideoxy-D-glycero-α-D-galacto-2-nonulopyranosylonic acid))-2-oxo-ethyl-1H-1,2,3-triazol-4-yl)methyl)amine (ME0385) and Tris ((1-(2-O-(5-N-acetamido-3,5-dideoxy-D-glycero-α-D-galacto-2-nonulopyranosylonic acid))-3-oxopropyl-1H-1,2,3-triazol-4-yl)methyl)amine (ME0386), proved straightforward and could be achieved in eight steps from commercially available chemicals or in five steps from key intermediate 1 (Scheme 1). The synthesis of the sialic acid thiophenyl derivative 1, readily prepared from commercial sialic acid, was performed according to published procedures (Marra et al Carbohydr. Res. 1989, 187, 35). The sialosides 3a and 3b were then accessed in good conversion by glycosylation of the corresponding alcohol (2-bromoethanol and 3-bromopropan-1-ol respectively) with compound 1. Using other bromoalcohols would provide building blocks with linkers with other lengths. The reaction yielded an inseparable mixture of anomers together with the resulting elimination product that were not further purified at this stage. Bromo derivatives 3a and 3b were readily converted to their azido analogues 5a and 5b. Subsequent O-deacylation using standard Zemplén conditions afforded anomerically pure 7a and 7b in 40% and 58% yields, respectively, over three steps. Then, compounds 7a and 7b were reacted with tripropargylamine in a copper-catalyzed azide-alkyne cycloaddition reaction ("click" reaction). Thus, methyl esters 9a and 9b were obtained in 51% and 45% yields, respectively. Subsequent saponification provided the final target compounds ME0385 and ME0386 in 76% and 41% yields, respectively.

Use of other ethyne derivatives than tripropargylamine in the copper-catalyzed azide-alkyne cycloaddition would provide access to other types of tri- or tetravalent sialic acid derivates.

Scheme 1. aSynthesis of ME0385 and ME-386

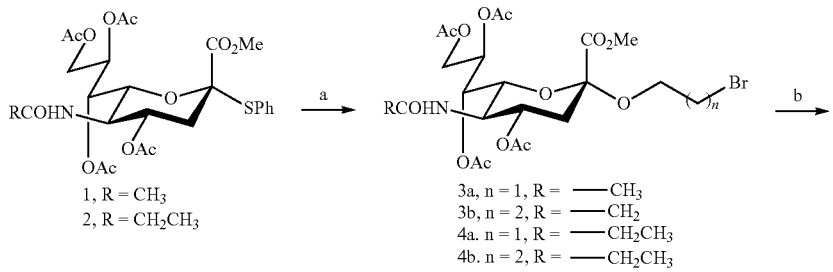

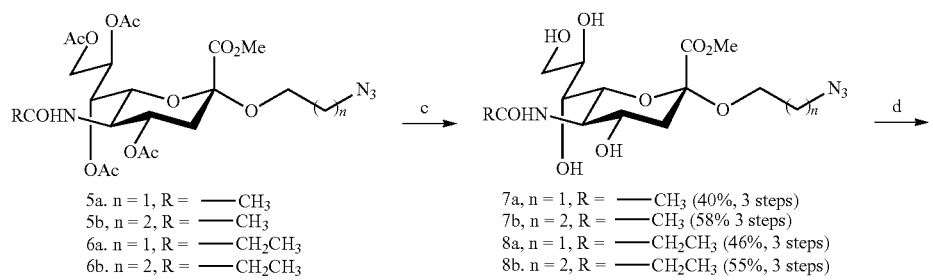

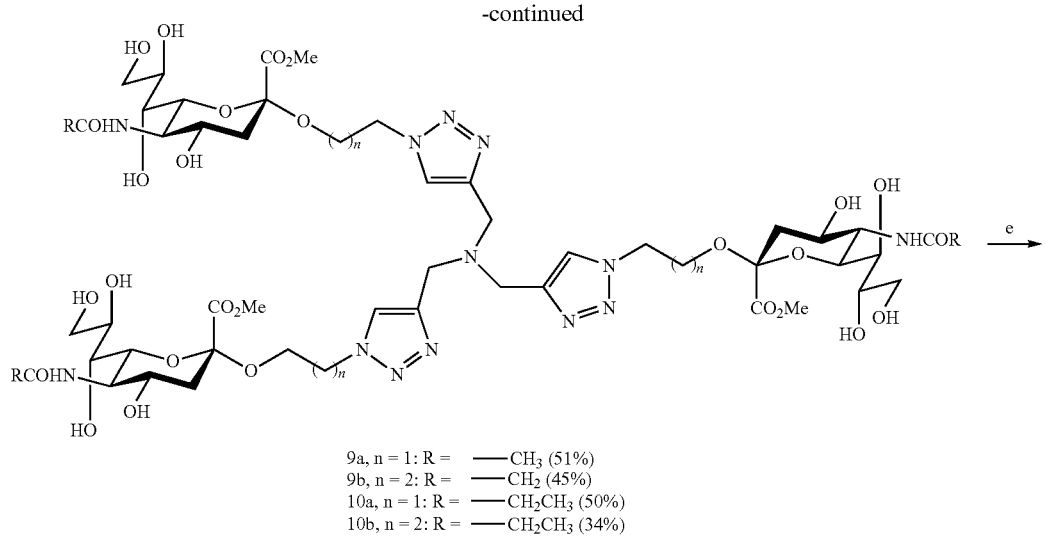

9a, n = 1: R = —CH₃ (51%)
9b, n = 2: R = —CH₂ (45%)
10a, n = 1: R = —CH₂CH₃ (50%)
10b, n = 2: R = —CH₂CH₃ (34%)

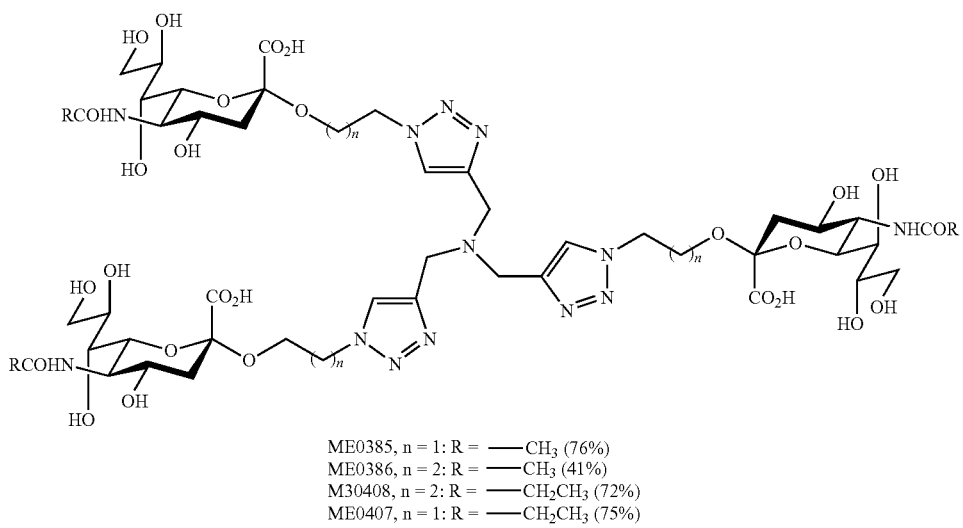

ME0385, n = 1: R = —CH₃ (76%)
ME0386, n = 2: R = —CH₃ (41%)
M30408, n = 2: R = —CH₂CH₃ (72%)
ME0407, n = 1: R = —CH₂CH₃ (75%)

[a]Reagents and conditions: (a) i: molecular sieves 3Å, 2-bromoethanol or 3-bromopropan-1-ol, CH₃CN/CH₂Cl₂ (3:2), rt, 2 h, ii: AgOTf, IBr, -73° C., 4.5 h, iii: DIPEA, -73° C., 30 min. (b) NaN₃, TBAI, DMSO, rt, 6 h. (c) i: NAOMe, MeOH, rt, 3 h, ii: H⁺ ion exchange resin. (d) Tripropargylamine, CuSO₄, sodium ascorbate, THF/H₂O (1:1), 50° C., 3 h then rt, 18 h. (e) i: LiOH, MeOH, rt, 9h, ii: H⁺ ion exchange resin.

The N-modified trivalent sialic acids Tris ((1-(2-O-(5-N-propanoylamido-3,5-dideoxy-D-glycero-α-D-galacto-2-nonulopyranosylonic acid))-2-oxoethyl-1H-1,2,3-triazol-4-yl)methyl)amine ME0408 and Tris ((1-(2-O-(5-N-propanoylamido-3,5-dideoxy-D-glycero-α-D-galacto-2-nonulopyranosylonic acid))-3-oxopropyl-1H-1,2,3-triazol-4-yl)methyl)amine ME0407 could be produced in 13 steps from commercially available sialic acid or five steps from key intermediate 2 (Scheme 1). The synthesis of compound 2 was performed according to published procedures (Johansson et al J. Med. Chem. 2009, 52, 3666). Next steps were analogous to the previously described synthetic route to compounds ME0385 and ME0386. Thus, the successive glycosylation, azide formation and O-deacylation reactions afforded anomerically pure product 8a and 8b in 46% and 55% yields over three steps, respectively. Subsequent "click" reaction provided the trivalent compounds 10a and 10b in 50% and 34% yields, respectively. Finally, saponification of the methyl esters 10a and 10b gave the target products ME0408 and ME0407 in good yields.

General Method for the Glycosylation Reaction.

Glycosyl donor 1 or 2 (1.0 equiv) and freshly crushed molecular sieves 3 Å (1.5 g/mmol) were dissolved/suspended in a mixture of CH₃CN/CH₂Cl₂ (3:2; 35 mL/mmol) at room temperature and under nitrogen atmosphere. 2-Bromoethanol or 3-bromopropan-1-ol (4.5 equiv) was added and the mixture was stirred for 2 h. The reaction was protected from light and a solution of silver triflate (2.0 equiv) in CH₃CN was added. The mixture was cooled to -73° C. (-70° C.<t<-75° C.) and IBr (1.4 equiv, 1M in CH₂Cl₂) was added. The reaction was allowed to proceed for 4.5 h at -73° C. After completion, DIPEA (6.0 equiv) was added. The reaction mixture was stirred for a further 30 min at -73° C. and then allowed to warm to room temperature. The mixture was filtered through a Celite® pad, washed with CH₂Cl₂ or CH₃CN and the solvents concentrated to dryness.

Methyl (2-bromoethoxy(5-N-acetamido-4,7,8,9-tetra-O-acetyl-3,5-dideoxy-D-glycero-α-D-galacto-2-nonylopyranosyl))-onate (3a)

Compound 3a was synthesized following the general method for the glycosylation reaction. Purification by column chromatography (gradient n-Heptane/EtOAc) afforded compound 3a and the corresponding reverse anomer. Compound 3a was used in the next step without additional purification.

Methyl (3-bromo-propyloxy(5-N-acetamido-4,7,8,9-tetra-O-acetyl-3,5-dideoxy-D-glycero-α-D-galacto-2-nonylopyranosyl))-onate (3b)

Compound 3b was synthesized following the general method for the glycosylation reaction. Purification by column chromatography (gradient n-Heptane/EtOAc) afforded compound 3b and the corresponding reverse anomer. Compound 3b was used in the next step without additional purification.

Methyl (2-bromoethoxy(5-N-propanoylamido-4,7,8,9-tetra-O-acetyl-3,5-dideoxy-D-glycero-α-D-galacto-2-nonylopyranosyl))-onate (4a)

Compound 4a was synthesized following the general method for the glycosylation reaction. Purification by column chromatography (Toluene/EtOH, 10:1) afforded compound 4a and the corresponding reverse anomer (390 mg, 95%; a/(3 (6:1)). Compound 4a was used in the next step without additional purification.

Methyl (3-bromo-propyloxy(5-N-propanoylamido-4,7,8,9-tetra-O-acetyl-3,5-dideoxy-D-glycero-α-D-galacto-2-nonylopyranosyl))-onate (4b)

Compound 4b was synthesized following the general method for the glycosylation reaction. Purification by column chromatography (Toluene/EtOH, 8:1) afforded compound 4b and the corresponding reverse anomer (400 mg, 98%; α/β (22:3)). Compound 4b was used in the next step without additional purification.

General Method for the Synthesis of Azido Derivatives.

To the bromo derivatives (1.0 equiv) dissolved in DMSO (40 mL/mmol) were successively added portion-wise sodium azide (6.0 equiv) and TBAI (2.0 equiv). The reaction was allowed to proceed for 6 h at room temperature and under nitrogen atmosphere. After completion, the mixture was diluted with $CH_2Cl_2$, washed with water and brine, dried over $MgSO_4$, filtered and concentrated to dryness.

Methyl (2-azidoethoxy(5-N-acetamido-4,7,8,9-tetra-O-acetyl-3,5-dideoxy-D-glycero-α-D-galacto-2-nonylopyranosyl))-onate (5a)

Compound 5a was synthesized following the general method for the synthesis of azido derivatives. Purification by column chromatography ($CH_2Cl_2$/MeOH, 95:5) afforded compound 5a and the corresponding reverse anomer (α/β (5:1)). Compound 5a was used in the next step without additional purification.

Methyl (3-azido-propyloxy(5-N-acetamido-4,7,8,9-tetra-O-acetyl-3,5-dideoxy-D-glycero-α-D-galacto-2-nonylopyranosyl))-onate (5b)

Compound 5b was synthesized following the general method for the synthesis of azido derivatives. Purification by column chromatography ($CH_2Cl_2$/MeOH, 95:5) afforded compound 5b and the corresponding reverse anomer (α/β (n.d.)). Compound 5b was used in the next step without additional purification.

Methyl (2-azidoethoxy(5-N-propanoylamido-4,7,8,9-tetra-O-acetyl-3,5-dideoxy-D-glycero-α-D-galacto-2-nonylopyranosyl))-onate (6a)

Compound 6a was synthesized following the general method for the synthesis of azido derivatives. Purification by column chromatography (Toluene/$CH_2Cl_2$/MeOH, 10:2:0.5) afforded compound 6a and the corresponding reverse anomer (366 mg, quantitative; a/(3 (6:1)). Compound 6a was used in the next step without additional purification.

Methyl (3-azido-propyloxy(5-N-propanoylamido-4,7,8,9-tetra-O-acetyl-3,5-dideoxy-D-glycero-α-D-galacto-2-nonylopyranosyl))-onate (6b)

Compound 6b was synthesized following the general method for the synthesis of azido derivatives. Purification by column chromatography (Toluene/$CH_2Cl_2$/MeOH, 8:2:0.5) afforded compound 6b and the corresponding reverse anomer (419 mg, quantitative; α/β (22:3)). Compound 6b was used in the next step without additional purification.

General Method for the 0-Deacylation of Sialosides.

To peracylated sialoside (1.0 equiv) dissolved in MeOH (70 mL) was added sodium methoxide (3.9 equiv). The reaction was allowed to proceed for 3 h at room temperature and under nitrogen atmosphere. After completion, the solution was neutralized by drop-wise addition of glacial AcOH or by Amberlyst® 15. The solvent was then concentrated to dryness.

Methyl (2-azidoethoxy(5-N-acetamido-3,5-dideoxy-D-glycero-α-D-galacto-2-nonylopyranosyl))-onate (7a)

Compound 7a was synthesized following the general method for the O-deacylation of sialosides. Purification by column chromatography (EtOAc/EtOH/$H_2O$, 4:1:0.1) afforded compound 7a (256 mg, 46% yield over three steps).

$^1$H NMR (400 MHz, $CD_3OD$): δ 3.93-4.02 (m, 1H, —$OCH_{2b}$—), 3.85 (s, 3H, $OCH_3$), 3.80-3.84 (m, 2H, H-8, H-9$_b$), 3.77 (t, $J_{5,4}$≈$J_{5,6}$=10.2 Hz, 1H, H-5), 3.60-3.73 (m, 3H, H-4, H-9$_a$, —$OCH_{2a}$), 3.58 (dd, $J_{6,5}$=10.7 and $J_{6,7}$=1.8 Hz, 1H, H-6), 3.51 (dd, $J_{7,8}$=8.7 and $J_{6,7}$=1.8 Hz, 1H, H-7), 3.27-3.43 (m, 2H, —$CH_2N_3$), 2.72 (dd, $J_{3eq,3ax}$=12.8 and $J_{3eq,4}$=4.6 Hz, 1H, H-3$_{eq}$), 2.00 (s, 3H, $COCH_3$), 1.77 (dd, $J_{3eq,3ax}$=12.8 and $J_{3ax,4}$=11.8 Hz, 1H, H-3$_{ax}$).

$^{13}$C NMR (100 MHz, $CD_3OD$): δ 175.22, 170.71, 100.20, 75.05, 72.37, 70.18, 68.49, 64.74, 64.47, 53.79, 53.42, 51.74, 41.57, 22.66.

ESI-MS m/z calcd for $C_{14}H_{26}N_4O_9$ $(M+H)^+$ 392.15 and $C_{14}H_{25}N_4NaO_9$ $(M+Na)^+$ 415.14. found 392.56 and 415.31 respectively.

Methyl (3-azido-propyloxy(5-Nacetamido-3,5-dideoxy-D-glycero-α-D-galacto-2-nonylopyranosyl))-onate (7b)

Compound 7b was synthesized following the general method for the O-deacylation of sialosides. Purification by column chromatography (EtOAc/EtOH/$H_2O$, 4:1:0.1) afforded compound 7b (289 mg, 55% yield over three steps).

¹H NMR (400 MHz, CD₃OD): δ 3.80-3.92 (m, 6H, —OCH$_{2b}$—, H-9$_b$, H-8, OCH₃), 3.77 (t, J$_{5,4}$≈J$_{5,6}$=10.2 Hz, 1H, H-5), 3.61-3.69 (m, 2H, H-9$_a$, H-4), 3.59 (dd, J$_{6,5}$=10.3 and J$_{6,7}$=2.0 Hz, 1H, H-6), 3.51 (dd, J$_{7,8}$=9.2 and J$_{6,7}$=1.9 Hz, 1H, H-7), 3.43-3.50 (m, 1H, OCH$_{2a}$), 3.38 (t, J=6.6 Hz, 2H, —CH₂N₃), 2.68 (dd, J$_{3eq,3ax}$=12.8 and J$_{3eq,4}$=4.7 Hz, 1H, H-3$_{eq}$), 2.00 (s, 3H, COCH₃), 1.75-1.85 (m, 2H, —CH₂—), 1.74 (dd, J$_{3eq,3ax}$=12.8 and J$_{3ax,4}$=11.8 Hz, 1H, H-3$_{ax}$).

¹³C NMR (100 MHz, CD₃OD): δ 175.22, 171.06, 100.21, 74.97, 72.45, 70.20, 68.52, 64.71, 62.09, 53.83, 53.38, 48.98, 41.69, 30.14, 22.65.

ESI-MS m/z calcd for C₁₅H₂₆N₄O₉ (M+H)⁺ 407.17 and C₁₅H₂₅N₄NaO₉ (M+Na)⁺ 429.16. found 406.87 and 428.56 respectively.

Methyl (2-azidoethoxy(5-N-propanoylamido-3,5-dideoxy-D-glycero-α-D-galacto-2-nonylopyranosyl))-onate (8a)

Compound 8a was synthesized following the general method for the O-deacylation of sialosides. Purification by column chromatography (Toluene/CH₂Cl₂/MeOH, 3.5:6:0.5 to 3:6:1) afforded compound 8a (120 mg, 46% yield over three steps).

¹H NMR (400 MHz, CD₃OD): δ 3.94-4.00 (m, 1H, —OCH$_{2b}$—), 3.85 (s, 3H, OCH₃), 3.80-3.84 (m, 2H, H-8, H-9), 3.77 (t, J$_{5,4}$≈J$_{5,6}$=10.4 Hz, 1H, H-5), 3.67-3.72 (ddd, J$_{4,3ax}$=11.6, J$_{5,4}$=10.4, J$_{4,3eq}$=4.6 Hz, 1H, H-4), 3.60-3.66 (m, 2H, H-9$_a$, —OCH$_{2a}$—), 3.57 (dd, J$_{6,5}$=10.2 and J$_{6,7}$=1.6 Hz, 1H, H-6), 3.49 (dd, J$_{7,8}$=8.9 and J$_{6,7}$=1.6 Hz, 1H, H-7), 3.32-3.35 (m, 1H, —CH$_{2b}$N₃), 2.72 (dd, J$_{3eq,3ax}$=12.8 and J$_{3eq,4}$=4.6 Hz, 1H, H-3$_{eq}$), 2.27 (q, J=7.6 Hz, 2H, —COCH₂—), 1.76 (dd, J$_{3eq,3ax}$=12.8 and J$_{3ax,4}$=11.6 Hz, 1H, H-3$_{ax}$), 1.14 (t, J=7.6 Hz, 3H, —COCH₂).

¹³C NMR (100 MHz, CD₃OD): δ 179.01, 170.73, 100.19, 75.09, 72.36, 70.17, 68.40, 64.72, 64.47, 53.64, 53.43, 51.73, 41.64, 30.16, 10.28.

ESI-MS m/z calcd for C₁₅H₂₇N₄O₉ (M+H)⁺ 407.18 and C₁₅H₂₆N₄NaO₉ (M+Na)⁺ 429.16. found 407.09 and 429.02 respectively.

Methyl (3-azido-propyloxy(5-N-propanoylamido-3,5-dideoxy-D-glycero-α-D-galacto-2-nonylopyranosyl))-onate (8b)

Compound 8b was synthesized following the general method for the O-deacylation of sialosides. Purification by column chromatography (Toluene/CH₂Cl₂/MeOH, 3.5:6:0.5 to 3:6:1) afforded compound 8b (157 mg, 55% yield over three steps).

¹H NMR (400 MHz, CD₃OD): δ 3.80-3.89 (m, 3H, —OCH$_{2b}$—, H-9$_b$, H-8), 3.84 (s, 3H, OCH₃), 3.76 (t, J$_{5,4}$≈J$_{5,6}$=10.2 Hz, 1H, H-5), 3.60-3.69 (m, 2H, H-9$_a$, H-4), 3.58 (dd, J$_{6,5}$=10.2 and J$_{6,7}$=1.6 Hz, 1H, H-6), 3.49 (dd, J$_{7,8}$=8.9 and J$_{6,7}$=1.6 Hz, 1H, H-7), 3.43-3.50 (m, 1H, OCH$_{2a}$—), 3.38 (t, J=6.6 Hz, 2H, —CH₂N₃), 2.68 (dd, J$_{3eq,3ax}$=12.8 and J$_{3eq,4}$=4.6 Hz, 1H, H-3$_{eq}$), 2.27 (q, J=7.6 Hz, 2H, —COCH₂—), 1.75-1.83 (m, 2H, —CH₂—), 1.74 (dd, J$_{3eq,3ax}$=12.8 and J$_{3ax,4}$=11.8 Hz, 1H, H-3$_{ax}$), 1.13 (t, J=7.6 Hz, 3H, COCH₂CH₃).

¹³C NMR (100 MHz, CD₃OD): δ 178.99, 171.08, 100.20, 75.01, 72.43, 70.18, 68.42, 64.69, 62.07, 53.68, 53.39, 48.78, 41.76, 30.16, 30.13, 10.28.

ESI-MS m/z calcd for C₁₆H₂₉N₄O₉ (M+H)⁺ 421.19 and C₁₆H₂₈N₄NaO₉ (M+Na)⁺ 443.18. found 420.99 and 442.93 respectively.

General Method for the Synthesis of Trivalent Sialic Acid.

To the azido derivative (3.7 equiv) dissolved in THF/H₂O (1:1, 81 mL/mmol) was successively added tripropargylamine (1.0 equiv), CuSO₄ (0.9 equiv) and sodium ascorbate (0.9 equiv). The reaction was allowed to proceed at 50° C. for 3 h and at room temperature for a further 18 h. After complete consumption of the starting azide, THF was evaporated under vacuum and the crude was freeze-dried. The crude solid was dissolved in DMSO and purified by HPLC (A: aq. 0.005% CF₃COOH in H₂O, B: aq. 0.005% CF₃COOH in CH₃CN, organic phase gradient 7% to 25%). The collected compound-containing fractions were freeze-dried to afford pure product.

Tris ((1-(2-O-((methyl (5-N-acetamido-3,5-dideoxy-D-glycero-α-D-galacto-2-nonylopyranosyl)-onate))-2-oxoethyl-, 2, 3-triazol-4-yl)methyl)amine (9a)

Compound 9a was synthesized following the general method for the synthesis of trivalent sialic acid (40 mg, 51% yield).

¹H NMR (400 MHz, CD₃OD): δ 8.08 (s, 3H, 3ArCH), 8.01 (d, J$_{5,NH}$=8.4 Hz, 3H, 3NH), 4.60 (t, J=5.0 Hz, 6H, 3-CH₂—ArN), 4.15-4.27 (m, 3H, 3-OCH$_{2b}$), 3.70-3.97 (m, 27H, 3-OCH$_{2a}$, 3H-9$_b$, —N(CH₂)₃, 3H-8, 3H-5, 3-OCH₃), 3.55-3.67 (m, 9H, 3H-4, 3H-9$_b$, 3H-6), 3.48 (dd, J$_{7,8}$=8.8 and J$_{6,7}$=1.4 Hz, 3H, H-7), 2.58 (dd, J$_{3eq,3ax}$=12.8 and J$_{3eq,4}$=4.7 Hz, 3H, 3H-3$_{eq}$), 1.99 (s, 9H, 3-COCH₃), 1.71 (dd, J$_{3eq,3ax}$=12.8 and J$_{3ax,4}$=11.7 Hz, 3H, 3H-3$_{ax}$).

¹³C NMR (100 MHz, CD₃OD): δ 175.12, 170.47, 144.25, 126.94, 100.28, 75.07, 72.25, 70.16, 68.40, 64.84, 63.91, 53.68, 53.55, 51.47, 48.73, 41.44, 22.70.

ESI-MS m/z calcd for C₅₁H₈₂N₁₃O₂₇ (M+H)⁺ 1308.54. found 1309.47.

Tris ((1-(2-O-(methyl (5-N-acetamido-3,5-dideoxy-D-glycero-α-D-galacto-2-nonylopyranosyl)-onate))-3-oxopropyl-1H-1,2,3-triazol-4,1-yl)methyl)amine (9b)

Compound 9b was synthesized following the general method for the synthesis of trivalent sialic acid (60 mg, 45% yield).

¹H NMR (400 MHz, CD₃OD): δ 8.01 (s, 3H, 3ArCH), 4.50 (t, J=6.6 Hz, 6H, 3-CH₂—ArN), 3.70-3.88 (m, 27H, 3-OCH$_{2b}$—, 3H-9$_b$, 3-OCH₃, —N(CH₂)₃, 3H-8, 3H-5), 3.54-3.69 (m, 9H, 3H-4, 3H-9$_b$, 3H-6), 3.49 (dd, J$_{7,8}$=9.0 and J$_{6,7}$=1.3 Hz, 3H, 3H-7), 3.35-3.43 (m, 3H, 3-OCH$_{2a}$), 2.68 (dd, J$_{3eq,3ax}$=12.8 and J$_{3eq,4}$=4.7 Hz, 3H, 3H-3$_{eq}$), 2.09-2.20 (m, 6H, 3-CH₂—), 2.00 (s, 9H, 3-COCH₃), 1.74 (dd, J$_{3eq,3ax}$=12.7 and J$_{3ax,4}$=11.8 Hz, 3H, 3H-3$_{ax}$).

¹³C NMR (100 MHz, CD₃OD): δ 175.20, 170.86, 145.26, 125.97, 100.12, 74.92, 72.43, 70.19, 68.50, 64.77, 61.77, 53.80, 53.54, 48.48, 48.10, 41.65, 31.29, 22.72.

ESI-MS m/z calcd for C₅₄H₈₈N₁₃O₂₇ (M+H)⁺ 1350.58. found 1350.21.

Tris((1-(2-O-(methyl (5-N-propanoylamido-3,5-dideoxy-D-glycero-α-D-galacto-2-nonylopyranosyl)-onate))-2-oxoethyl-1H-1, 2, 3-triazol-4-yl)methyl)amine (10a)

Compound 10a was synthesized following the general method for the synthesis of trivalent sialic acid (60 mg, 50% yield).

¹H NMR (400 MHz, CD₃OD): δ 8.04 (s, 3H, 3ArCH), 4.50 (t, J=5.1 Hz, 6H, 3-CH₂—ArN), 4.16-4.23 (m, 3H,

3-OCH$_{2b}$), 3.86-3.92 (m, 3H, 3-OCH$_{2a}$), 3.74-3.84 (m, 15H, 3H-9$_b$, —N(CH$_2$)$_3$, 3H-8, 3H-5), 3.72 (s, 9H, 3-OCH$_3$), 3.59-3.67 (m, 6H, 3H-4, 3H-9$_b$), 3.57 (dd, J$_{6,5}$=10.4 and J$_{6,7}$=1.3 Hz, 3H, 3H-6), 3.47 (dd, J$_{7,8}$=8.9 and J$_{6,7}$=1.3 Hz, 3H, H-7), 2.58 (dd, J$_{3eq,3ax}$=12.4 and J$_{3eq,4}$=4.6 Hz, 3H, 3H-3$_{eq}$), 2.25 (q, J=7.6 Hz, 6H, 3-COCH$_2$—), 1.74 (appear as t, J$_{3eq,3ax}$≈J$_{3ax,4}$=12.4 Hz, 3H, 3H-3$_{ax}$), 1.12 (t, J=7.6 Hz, 9H, 3-COCH$_2$CH$_3$).

$^{13}$C NMR (100 MHz, CD$_3$OD): δ 178.88, 170.43, 145.08, 126.66, 100.23, 75.04, 72.15, 69.97, 68.29, 64.73, 63.95, 53.60, 53.45, 51.43, 49.07, 41.52, 31.15, 10.36.

ESI-MS m/z calcd for C$_{54}$H$_{88}$N$_{13}$O$_{27}$ (M+H)$^+$ 1350.59. found 1351.56.

Tris ((1-(2-O-(methyl (5-N-propanoylamido-3,5-dideoxy-D-glycero-α-D-galacto-2-nonylopyranosyl)-onate))-3-oxopropyl-1H-1, 2, 3-triazol-4-yl) methyl)amine (10b)

Compound 10b was synthesized following the general method for the synthesis of trivalent sialic acid (45 mg, 34% yield).

$^1$H NMR (400 MHz, CD$_3$OD): δ 8.03 (s, 3H, 3ArCH), 7.89 (d, J$_{5,NH}$=8.5 Hz, 3H, 3NH), 4.50 (t, J=6.5 Hz, 6H, 3-CH$_2$—ArN), 3.73-3.86 (m, 18H, 3-OCH$_{2b}$—, 3H-9$_b$, —N(CH$_2$)$_3$, 3H-8, 3H-5), 3.81 (s, 9H, 3-OCH$_3$), 3.58-3.70 (m, 6H, 3H-4, 3H-9$_b$), 3.56 (dd, J$_{6,5}$=10.4 and J$_{6,7}$=1.3 Hz, 3H, 3H-6), 3.47 (dd, J$_{7,8}$=8.9 and J$_{6,7}$=1.3 Hz, 3H, 3H-7), 3.35-3.43 (m, 3H, 3-OCH$_{2a}$), 2.68 (dd, J$_{3eq,3ax}$=12.4 and J$_{3eq,4}$=4.6 Hz, 3H, 3H-3$_{eq}$), 2.27 (q, J=7.6 Hz, 6H, 3-COCH$_2$—), 2.10-2.20 (m, 6H, 3-CH$_2$—), 1.74 (appear as t, J$_{3eq,3ax}$≈J$_{3ax,4}$=12.4 Hz, 3H, 3H-3$_{ax}$), 1.13 (t, J=7.6 Hz, 9H, 3-COCH$_2$CH$_3$).

$^{13}$C NMR (100 MHz, CD$_3$OD): δ 178.92, 170.88, 143.82, 126.16, 100.12, 75.01, 72.44, 70.22, 68.44, 64.72, 61.73, 53.67, 53.52, 49.28, 49.07, 41.75, 31.28, 30.17, 10.32.

ESI-MS m/z calcd for C$_{57}$H$_{94}$N$_3$O$_{27}$ (M+H)$^+$ 1392.64 and C$_{57}$H$_{93}$N$_{13}$NaO$_{27}$ (M+Na)$^+$ 1414.62. found 1392.50 and 1414.47 respectively.

General Method for Saponification of Methyl Ester.

To the trivalent methyl ester derivatives (1.0 equiv) dissolved in MeOH (135 mL/mmol) was added an aqueous solution of LiOH (1M, 9.0 equiv). The mixture was allowed to proceed for 9 h at room temperature. After completion, the reaction mixture was neutralized with Dowex 50W8 (H$^+$). After removal of the Dowex resin, the solvent was evaporated under vacuum and the crude, dissolved in water, was eluted on a C-18 plug with H$_2$O. The compound-containing fractions were freeze-dried to yield pure trivalent sialic acid derivative.

Tris ((1-(2-O-(5-N-acetamido-3,5-dideoxy-D-glycero-α-D-galacto-2-nonylopyranosylonic acid))-2-oxoethyl-1H-1,2,3-triazol-4-yl)methyl)amine (ME0385)

ME0385 was synthesized following the general method for the saponification of methyl ester (22 mg, 76% yield). [α]$_D^{20}$ −15.77 (c 4.8 mg/mL, H$_2$O).

$^1$H NMR (400 MHz, D$_2$O): δ 8.40 (s, 3H, 3ArCH), 4.72 (t, J=5.2 Hz, 6H, 3-CH$_2$—ArN), 4.60 (bs, 6H, —N(CH$_2$)$_3$), 4.14-4.27 (m, 3H, 3-OCH$_{2b}$), 3.93-4.02 (m, 3H, 3-OCH$_{2a}$), 3.85 (dd, J$_{9a,9b}$=11.7 and J$_{9b,8}$=2.3 Hz 3H, 3H-9$_b$), 3.73-3.82 (m, 6H, 3H-8, 3H-5), 3.59-3.72 (m, 9H, 3H-4, 3H-6, 3H-9$_a$), 3.56 (dd, J$_{7,8}$=9.3 and J$_{6,7}$=1.7 Hz, 3H, H-7), 2.66 (dd, J$_{3eq,3ax}$=12.5 and J$_{3eq,4}$=4.6 Hz, 3H, 3H-3$_{eq}$), 2.04 (s, 9H, 3-COCH$_3$), 1.67 (appear as t, J$_{3eq,3ax}$≈J$_{3ax,4}$=12.0 Hz, 3H, 3H-3$_{ax}$).

$^{13}$C NMR (100 MHz, D$_2$O): δ 175.05, 172.55, 135.87, 128.64, 100.05, 72.72, 71.42, 68.10, 67.88, 62.68, 62.58, 51.73, 50.57, 46.49, 39.64, 22.0.

ESI-MS m/z calcd for C$_{48}$H$_{76}$N$_{13}$O$_{27}$ (M+H)$^+$ 1266.49. found 1266.29.

Tris ((1-(2-O-(5-N-acetamido-3,5-dideoxy-D-glycero-α-D-galacto-2-nonylopyranosylonic acid))-3-oxopropyl-1H-1,2,3-triazol-4-yl)methyl)amine (ME0386)

ME0386 was synthesized following the general method for the saponification of methyl ester (27 mg, 75% yield). [α]$_D^{20}$ −3.83 (c 3.9 mg/mL, H$_2$O).

$^1$H NMR (400 MHz, D$_2$O): δ 8.02 (s, 3H, 3ArCH), 4.45-4.64 (m, 6H, 3-CH$_2$—ArN), 3.92 (bs, 6H, N(CH$_2$)$_3$), 3.56-3.87 (m, 24H, 3H-9$_b$, 3-OCH$_2$—, 3H-8, 3H-5, 3H-4, 3H-6, 3H-9$_a$), 3.46-3.54 (m, 3H, 3H-7), 2.73 (dd, J$_{3eq,3ax}$=12.5 and J$_{3eq,4}$=4.7 Hz, 3H, 3H-3$_{eq}$), 2.15-2.25 (m, 6H, 3-CH$_2$—), 2.05 (s, 9H, COCH$_3$), 1.63 (appear as t, J$_{3eq,3ax}$≈J$_{3ax,4}$=12.1 Hz, 3H, 3H-3$_{ax}$).

$^{13}$C NMR (100 MHz, D$_2$O): δ 175.05, 173.52, 142.34, 125.79, 100.48, 72.56, 71.71, 68.28, 68.16, 62.51, 61.22, 51.89, 47.54, 47.30, 40.29, 29.64, 22.02.

ESI-MS m/z calcd for C$_{51}$H$_{82}$N$_{13}$O$_{27}$ (M+H)$^+$ 1308.54. found 1308.51.

Tris ((1-(2-O-(5-N-propanoylamido-3,5-dideoxy-D-glycero-α-D-galacto-2-nonylopyranosylonic acid))-2-oxoethyl-1H-1,2,3-triazol-4-yl)methyl)amine (ME0408)

ME0408 was synthesized following the general method for the saponification of methyl ester (19 mg, 72% yield). [α]$_D^{20}$ −14.34 (c 4.6 mg/mL, H$_2$O).

$^1$H NMR (400 MHz, D$_2$O): δ 8.17 (s, 3H, 3ArCH), 4.64 (bs, 6H, 3-CH$_2$—ArN), 4.07-4.20 (m, 9H, 3-OCH$_{2b}$, —N(CH$_2$)$_3$), 3.87-3.93 (m, 3H, 3-OCH$_{2a}$), 3.82 (dd, J$_{9a,9b}$=11.7 and J$_{9b,8}$=2.4 Hz 3H, 3H-9$_b$), 3.75 (ddd, J$_{8,7}$=8.9, J$_{8,9a}$=5.6 Hz, J$_{9b,8}$=2.4 Hz 3H, 3H-8), 3.72 (t, J$_{5,6}$≈J$_{5,4}$=10.1 Hz, 3H, 3H-5), 3.63-3.69 (m, 3H, 3H-4), 3.56-3.63 (m, 6H, 3H-6, 3H-9$_a$), 3.51 (dd, J$_{7,8}$=8.9 and J$_{6,7}$=1.6 Hz, 3H, H-7), 2.66 (dd, J$_{3eq,3ax}$=12.3 and J$_{3,q,4}$=4.6 Hz, 3H, 3H-3$_{eq}$), 2.28 (q, J=7.6 Hz, 6H, 3-COCH$_2$—), 1.74 (appear as t, J$_{3eq,3ax}$≈J$_{3ax,4}$=12.3 Hz, 3H, 3H-3$_{ax}$), 1.10 (t, J=7.6 Hz, 9H, 3-COCH$_2$CH$_3$).

$^{13}$C NMR (100 MHz, D$_2$O): δ 179.90, 174.12, 127.82, 101.35, 73.50, 72.50, 69.00, 68.91, 63.74, 63.40, 52.51, 51.39, 49.84, 40.87, 30.05, 10.36.

ESI-MS m/z calcd for C$_{51}$H$_{82}$N$_{13}$O$_{27}$ (M+H)$^+$ 1308.54. found 1308.44.

Tris ((1-(2-O-(5-N-propanoylamido-3,5-dideoxy-D-glycero-α-D-galacto-2-nonylopyranosylonic acid)-3-oxopropyl-1H-1,2,3-triazol-4-yl)methyl)amine (ME0407)

ME0407 was synthesized following the general method for the saponification of methyl ester (27 mg, 75% yield). [α]$_D^{20}$ −0.76 (c 4.8 mg/mL, H$_2$O).

$^1$H NMR (400 MHz, D$_2$O): δ 8.31 (s, 3H, 3ArCH), 4.53-4.63 (m, 12H, 3-CH$_2$—ArN, N(CH$_2$)$_3$), 3.82 (dd, J$_{9b,9a}$=11.8 and J$_{9b,8}$=2.4 Hz, 3H, H-9$_b$), 3.74-3.83 (m, 12H, 3-OCH$_{2b}$—, 3H-8, 3H-5), 3.67-3.73 (m, 3H, 3H-4), 3.67 (dd, J$_{6,5}$=10.4 and J$_{6,7}$=1.5 Hz, 3H, 3H-6), 3.60 (dd, J$_{9a,9b}$=11.8 and J$_{9a,8}$=5.9 Hz, 3H, 3H-9$_a$), 3.53 (dd, J$_{7,8}$=8.9 and J$_{6,7}$=1.5 Hz, 3H, 3H-7), 3.42-3.50 (m, 3H, 3-OCH$_{2a}$), 2.69 (dd, J$_{3eq,3ax}$=12.4 and J$_{3eq,4}$=4.5 Hz, 3H, 3H-3$_{eq}$), 2.29 (q, J=7.6 Hz, 6H, 3-COCH$_2$—), 2.15-2.25 (m, 6H, 3-CH$_2$—), 1.65 (appear as t, J$_{3eq,3ax}$≈J$_{3ax,4}$=12.4 Hz, 3H, 3H-3$_{ax}$), 1.11 (t, J=7.6 Hz, 9H, 3-COCH$_2$CH$_3$).

$^{13}$C NMR (100 MHz, D$_2$O): δ 178.87, 173.77, 136.66, 128.98, 100.86, 73.47, 72.34, 69.04, 68.66, 63.47, 61.82, 52.52, 48.52, 47.57, 40.83, 30.17, 30.01, 10.30.

ESI-MS m/z calcd for C$_{54}$H$_{88}$N$_{13}$O$_{27}$ (M+H)$^+$ 1350.59. found 1350.28.

Example 2

Use of Tris (2-azidoethyl)amine as Core Moiety

The route to N-Acyl trivalent sialic acids, such as Tris ((4-(2-O-(5-N-acetamido-3,5-dideoxy-D-glycero-α-D-galacto-2-nonulopyranosylonic acid))-2-oxoethyl-1H-1,2,3-triazol-1-yl)ethyl)amine (ME0461) and Tris ((4-(2-O-(5-N-acetamido-3,5-dideoxy-D-glycero-α-D-galacto-2-nonulopyranosylonic acid))-2-oxomethyl-1H-1,2,3-triazol-1-yl)ethyl)amine (ME0462), proved straightforward and could be achieved in seven steps from commercially available chemicals or in four steps from key intermediate 1 (Scheme 2). The synthesis of the sialic acid thiophenyl derivative 1, readily prepared from commercial sialic acid, was performed according to published procedures (Marra et al Carbohydr. Res. 1989, 187, 35). The sialosides 11a and 11b were accessed in moderate conversion by glycosylation of the corresponding alcohol (propargyl alcohol and 3-butyn-1-ol respectively) with compound 1. Using other alkyne alcohols would provide building blocks with linkers with other lengths. The reaction yielded an inseparable mixture of anomers together with the resulting elimination product that were not further purified at this stage.

Subsequent O-deacylation using standard Zemplén conditions afforded anomerically pure 12a and 12b in 48% and 31% yields, respectively, over two steps.

Then, compounds 12a and 12b were reacted with Tris (2-azidoethyl)amine (13) in a copper-catalyzed azide-alkyne cycloaddition reaction ("click" reaction).

Tris azido derivative 13 was synthesized in two steps from commercially available triethanolamine. First, triethanolamine was converted to tris (2-chloroethyl)amine according to published procedure (M. Sun et al *J. Am. Chem. Soc.* 2012, 134(51), 20581). Then, the chloro derivative was readily converted to its azido analogue 13 (Note: 13 is highly explosive, therefore it is critical to always store it in solution and in the dark). Methyl esters 14a and 14b were obtained in 76% and 53% yields, respectively.

Subsequent saponification provided the final target compounds ME0462 and ME0461 in quantitative and 88% yields, respectively.

Scheme 2. aSynthesis of ME0462 and ME0461

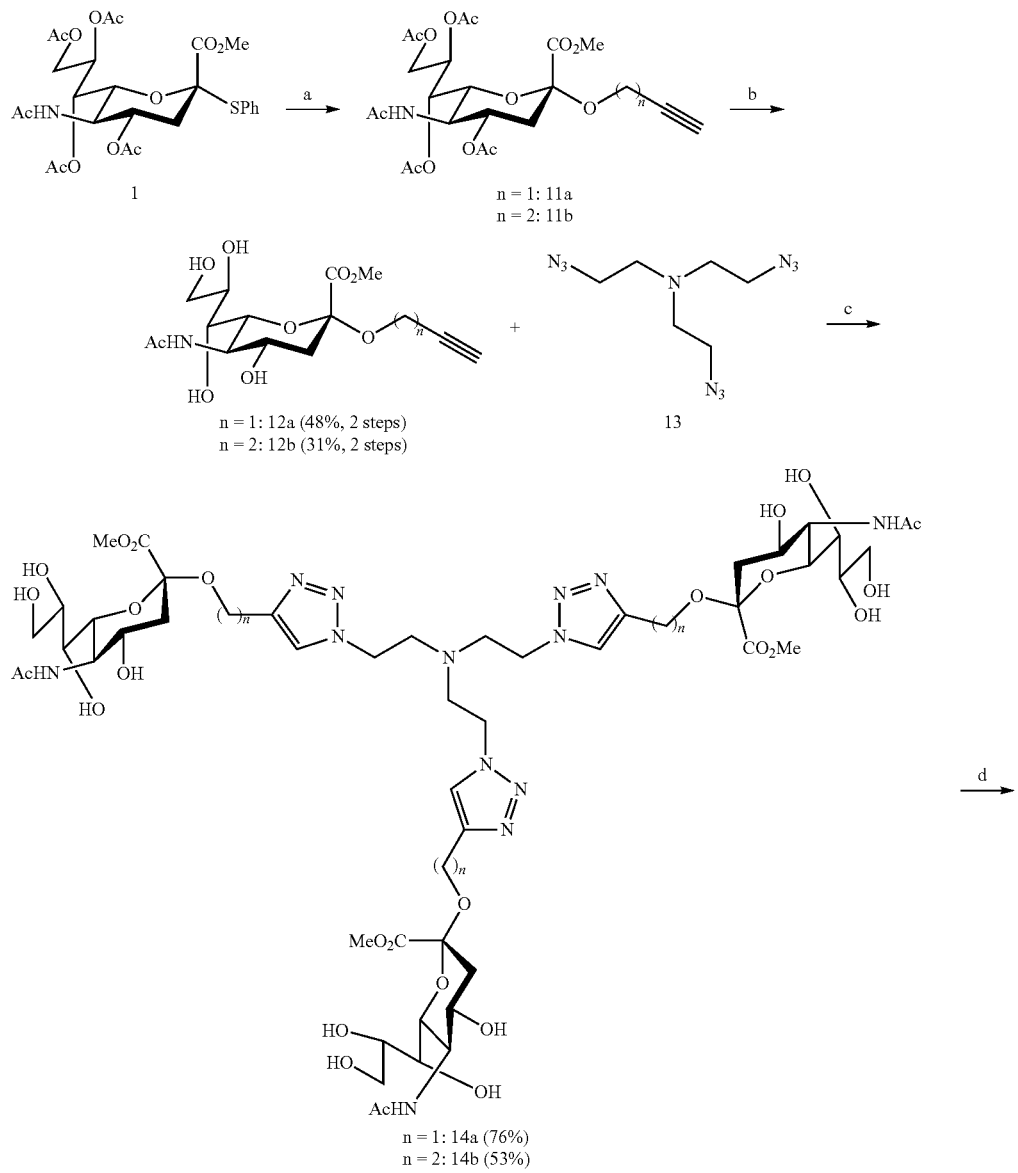

-continued

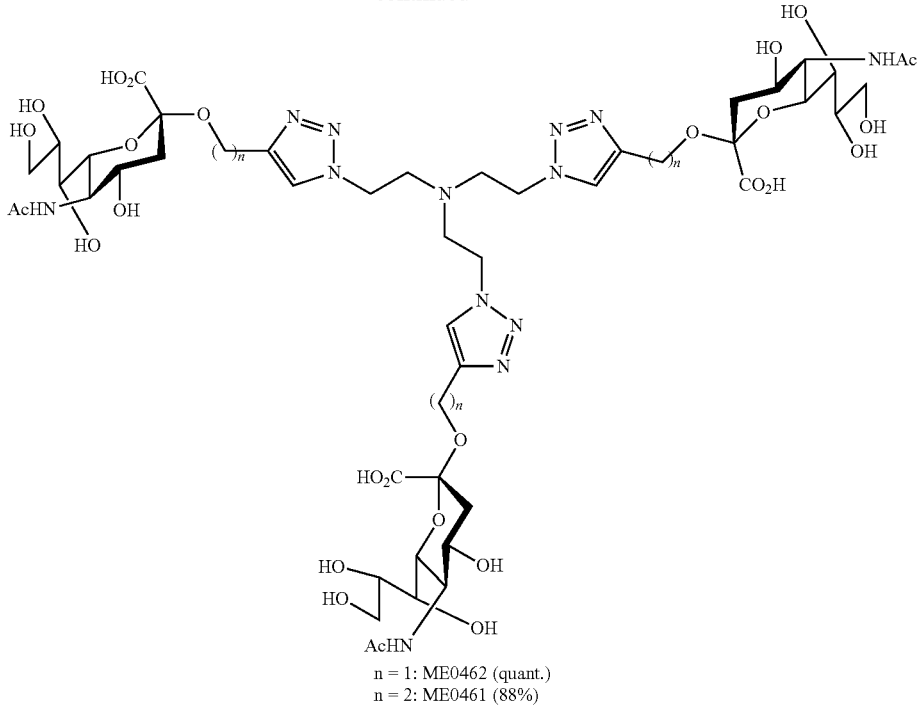

n = 1: ME0462 (quant.)
n = 2: ME0461 (88%)

<sup>a</sup>Reagents and conditions: (a) i: molecular sieves 3Å, 3-butyn-1-ol or propargyl alcohol, CH$_3$CN/CH$_2$Cl$_2$ (3:2), rt, 2 h, ii: AgOTf, IBr, -73° C., 4.5 h, iii: DIPEA, -73° C., 30 min. (b) i: NAOMe, MeOH, rt, 3 h, ii: H$^+$ ion exchange resin. (c) CuSO$_4$, sodium ascorbate, THF/H$_2$O (1:1), 50° C., 3 h then rt, 18 h. (d) i: LiOH, MeOH, rt, 9 H, ii: H$^+$ ion exchange resin.

General Method for the Glycosylation Reaction.

Glycosyl donor 1 (1.0 equiv) and freshly crushed molecular sieves 3 Å (1.5 g/mmol) were dissolved/suspended in a mixture of CH$_3$CN/CH$_2$Cl$_2$ (3:2; 35 mL/mmol) at room temperature and under nitrogen atmosphere. 3-Butyn-1-ol or propargyl alcohol (4.5 equiv) was added and the mixture was stirred for 2 h. The reaction was protected from light and a solution of silver triflate (2.0 equiv) in CH$_3$CN was added. The mixture was cooled to -73° C. (-70° C.<t<-75° C.) and IBr (1.4 equiv, 1M in CH$_2$Cl$_2$) was added. The reaction was allowed to proceed for 4.5 h at -73° C. After completion, DIPEA (6.0 equiv) was added. The reaction mixture was stirred for a further 30 min at -73° C. and then allowed to warm to room temperature. The mixture was filtered through a Celite® pad, washed with CH$_2$Cl$_2$ or CH$_3$CN and the solvents concentrated to dryness.

Methyl 2-(prop-2-ynyloxy(5-N-acetamido-4, 7, 8,9-tetra-O-acetyl-3,5-dideoxy-D-glycero-α-D-galacto-2-nonulopyranosyl))-onate (11a)

Compound 11a was synthesized following the general method for the glycosylation reaction. Purification by column chromatography (gradient n-Heptane/EtOAc) afforded compound 11a and the corresponding reverse anomer. Compound 11a was used in the next step without additional purification.

Methyl 2-(but-3-ynyloxy(5-N-acetamido-4,7,8,9-tetra-O-acetyl-3,5-dideoxy-D-glycero-α-D-galacto-2-nonulopyranosyl))-onate (11b)

Compound 11b was synthesized following the general method for the glycosylation reaction. Purification by column chromatography (gradient n-Heptane/EtOAc) afforded compound 11b and the corresponding reverse anomer. Compound 11b was used in the next step without additional purification.

General Method for the 0-Deacylation of Sialosides.

To peracylated sialoside (1.0 equiv) dissolved in MeOH (70 mL) was added sodium methoxide (3.9 equiv). The reaction was allowed to proceed for 3 h at room temperature and under nitrogen atmosphere. After completion, the solution was neutralized by drop-wise addition of glacial AcOH or by Amberlyst® 15. The solvent was then concentrated to dryness.

Methyl 2-(prop-2-ynyloxy(5-N-acetamido-3,5-dideoxy-D-glycero-α-D-galacto-2-nonulopyranosyl))-onate (12a).

Compound 12a was synthesized following the general method for the O-deacylation of sialosides. Purification by HPLC (A: aq. 0.005% HCOOH in H$_2$O, B: aq. 0.005% HCOOH in CH$_3$CN, organic phase gradient 5% to 20%) afforded compound 12a (178 mg, 48% yield over two steps).

$^1$H NMR (400 MHz, CD$_3$OD): δ 4.40 (dd, J=4.3 Hz, J=15.9 Hz, 1H), 4.33 (dd, J=4.3 Hz, J=15.9 Hz, 1H), 3.81-3.91 (m, 5H), 3.78 (d, J=10.3 Hz, 1H), 3.63-3.72 (m, 2H), 3.60 (dd, J=1.5 Hz, J=10.4 Hz, 1H), 3.52 (dd, J=1.4 Hz, J=9.0 Hz, 1H), 2.86 (t, J=2.4 Hz, 1H), 2.72 (dd, J$_{3eq,4}$=4.6 Hz, J$_{3eq,3ax}$=12.7 Hz, 1H), 2.01 (s, 3H), 1.75 (dd, J$_{3eq,3ax}$=12.7 Hz, J$_{3ax,4}$=11.8 Hz, 1H).

Methyl 2-(but-3-ynyloxy(5-N-acetamido-3,5-dideoxy-D-glycero-α-D-galacto-2-nonulopyranosyl)-onate (12b).

Compound 12b was synthesized following the general method for the O-deacylation of sialosides. Purification by column chromatography (EtOAc/EtOH/H$_2$O, 4:1:0.1) afforded compound 12b (218 mg, 31% yield over two steps).

¹H NMR (360 MHz, CD₃OD): δ 3.72-3.95 (m, 7H), 3.45-3.71 (m, 6H), 2.69 (dd, $J_{3eq,4}$=4.6 Hz, $J_{3eq,3ax}$=12.8 Hz, 1H), 2.35-2.45 (m, 2H), 2.26 (t, J=2.7 Hz, 1H) 2.00 (s, 3H), 1.73 (dd, $J_{3eq,3ax}$=12.3 Hz, $J_{3ax,4}$=12.0 Hz, 1H).

Tris (2-azidoethyl)amine (13)

A solution of triethanolamine (0.298 g, 2.0 mmol) in 0.5 mL of CHCl₃ was slowly added into a solution of thionyl chloride (0.52 mL, 7.0 mmol) in 0.8 mL of CHCl₃ with stirring. After addition, the reaction mixture was heated to reflux temperature for 4 hour. After cooling to room temperature the white solid product was filtered and washed with dichloromethane (1.0 mL×2) to give tris (2-chloroethyl)amine hydrochloride in 0.395 g (82%) yield after dried in vacuum over night. Following, Tris (2-chloroethyl)amine hydrochloride (0.198 g, 0.82 mmol) and sodium azide (0.320 g, 4.92 mmol) were added to DMSO (7.0 mL) and resulting mixture was stirred at 92° C. for 22 hour. After cooling the mixture was poured in to distilled water (40.0 mL) and the solution was alkalized with Na₂CO₃ (10% aq.) to pH=10, extracted with dichloromethane (15.0 mL×3). The organic phase was washed with water (20.0 mL) and then dried over Na₂SO₄. The dichloromethane was concentrated to 1 mL, and then 15.0 mL of THF was added, concentrated again to 1.0 mL, 15.0 mL of THF added and concentrated to 1.8 mL. This THF solution containing 0.8 mmol of tris (2-azidoethyl)amine could be used in next step. (Note: 13 is highly explosive, therefore it is critical to always store it in solution and the dark).

¹H NMR (400 MHz, CDCl₃): δ 3.33 (t, J=6.2 Hz, 6H), 2.76 (t, J=6.2 Hz, 6H).

ESI-MS m/z calcd for $C_6H_{13}N_{10}$ (M+H)⁺ 225.13. found 225.33.

Ref. M. Sun, C.-Y. Hong, C.-Y. Pan, *Journal of the American Chemical society* 2012, 134(51), 20581-20584.

Tris ((4-(2-O-(methyl (5-N-acetamido-3,5-dideoxy-D-glycero-α-D-galacto-2-nonulopyranosyl)-onate))-2-oxomethyl-1H-1, 2, 3-triazol-1-yl)ethyl)amine (14a)

To a solution of tris (2-azidoethyl)amine (0.075 mL, 0.033 mmol) in 1:1 mixture of water (1.7 mL) and THF (1.7 mL) were added methyl 2-(prop-2-ynyloxy(5-N-acetamido-3,5-dideoxy-D-glycero-α-D-galacto-2-nonulopyranosyl))-onate (0.0538 g, 0.149 mmol), sodium ascorbate (5.9 mg, 0.030 mmol) and copper(II) sulfate (4.8 mg, 0.030 mmol) while stirring. The mixture was first heated at 50° C. for 3.5 hour and at room temperature for additional 18 hour. After evaporation of THF under reduced pressure the residue was diluted to 2.6 mL with distilled water and then purified with preparative HPLC (A: aq. 0.005% HCOOH in H₂O, B: 0.005% HCOOH in CH₃CN, organic phase gradient 5% to 20%/30 min.) to give white product in 76% yields after lyophilization.

¹H NMR (400 MHz, CDCl₃): δ 7.78 (s, 3H), 4.92 (d, J=12.6 Hz, 3H), 4.64 (d, J=12.1 Hz, 3H), 4.30 (t, J=6.2 Hz, 6H), 3.79-3.93 (m, 18H), 3.60-3.74 (m, 9H), 3.47-3.58 (m, 3H), 3.03 (t, J=5.9 Hz, 6H), 2.67 (dd, $J_{3eq,4}$=4.6 Hz, $J_{3eq,3ax}$=12.8 Hz 3H), 2.00 (s, 9H), 1.74 (t, $J_{3eq,3ax}$=12.3 Hz, 3H).

¹³C NMR (100 MHz, CD₃OD): δ 175.05, 170.75, 145.52, 126.09, 100.06, 74.98, 72.26, 70.33, 68.53, 64.93, 58.51, 55.09, 53.71, 53.59, 41.65, 22.75.

ESI-MS m/z calcd for $C_{51}H_{82}N_3O_{27}$ (M+H)⁺ 1308.54. found 1309.13.

Tris ((4-(2-O-(methyl (5-N-acetamido-3,5-dideoxy-D-glycero-α-D-galacto-2-nonulopyranosyl)-onate))-2-oxoethyl-1H-1,2,3-triazol-1-yl)ethyl)amine (14b)

To a solution of tris (2-azidoethyl)amine (0.113 mL, 0.05 mmol) in 1:1 mixture of water (2.5 mL) and THF (2.5 mL) were added methyl 2-(but-3-ynyloxy(5-N-acetamido-3,5-dideoxy-D-glycero-α-D-galacto-2-nonulopyranosyl))-onate (0.0845 g, 0.225 mmol), sodium ascorbate (8.9 mg, 0.0449 mmol) and copper(II) sulfate (7.2 mg, 0.0451 mmol) while stirring. The mixture was first heated at 50° C. for 3.5 hour and at room temperature for additional 18 hour. After evaporation of THF under reduced pressure the residue was diluted to 3.0 mL with distilled water and then purified with preparative HPLC (A: aq. 0.005% HCOOH in H₂O, B: 0.005% HCOOH in CH₃CN, organic phase gradient 5% to 20%/30 min.) to give 35.9 mg (53.2%) white product after lyophilization.

¹H NMR (400 MHz, CD₃OD): δ 8.02 (d, J=8.5 Hz, 3H), 7.66 (s, 3H), 4.30 (t, J=5.9 Hz, 6H), 4.06 (dt, J=9.3 Hz, J=6.5 Hz, 3H), 3.74-3.87 (m, 18H), 3.57-3.72 (m, 12H), 3.50 (dd, J=1.2 Hz, J=8.7 Hz, 3H), 3.04 (t, J=5.7 Hz, 6H), 2.93 (t, J=6.1 Hz, 6H), 2.65 (dd, $J_{3eq,4}$=4.6 Hz, $J_{3eq,3ax}$=12.7 Hz, 3H), 2.00 (s, 9H), 1.72 (t, $J_{3eq,3ax}$=12.3 Hz, 3H).

¹³C NMR (100 MHz, CD₃OD): δ 175.16, 170.90, 146.05, 124.81, 100.22, 74.94, 72.44, 70.25, 68.52, 64.86, 64.05, 54.85, 53.80, 53.48, 41.74, 27.27, 22.72. ESI-MS m/z calcd for $C_{54}H_{88}N_{13}O_{27}$ (M+H)⁺ 1350.59. found 1351.70.

Tris ((4-(2-O-(5-N-acetamido-3,5-dideoxy-D-glycero-α-D-galacto-2-nonulopyranosylonic acid))-2-oxomethyl-1H-1,2,3-triazol-1-yl)ethyl)amine (ME0462)

Methyl ester (14a) obtained above was dissolved in MeOH (1.9 mL) and LiOH (0.15 mL, 1.0M) solutions. The mixture was stirred at room temperature for 44 hour, followed by LCMS, neutralized with amberlite IR120 to pH=7.0, concentrated and lyophilized to give 20.2 mg white product. $[α]_D^{20}$ −11.7 (c 1.0 mg/mL, H₂O).

¹H NMR (400 MHz, D₂O): δ 7.84 (s, 3H), 4.85 (d, J=12.0 Hz, 3H), 4.61 (d, J=12.0 Hz, 3H), 4.35 (t, J=6.0 Hz, 6H), 3.77-3.94 (m, 9H), 3.49-3.76 (m, 12H), 3.04 (t, J=6.0 Hz, 6H), 2.73 (dd, $J_{3eq,4}$=4.5 Hz, $J_{3eq,3ax}$=12.4 Hz, 3H), 2.03 (s, 9H), 1.66 (t, $J_{3eq,3ax}$=12.3 Hz, 3H).

¹³C NMR (100 MHz, D₂O): δ 174.99, 173.20, 143.93, 125.23, 100.66, 72.64, 71.61, 68.25, 68.21, 62.58, 57.31, 52.67, 51.81, 48.17, 40.23, 22.00.

ESI-MS m/z calcd for $C_{48}H_{76}N_{13}O_{27}$ (M+H)⁺ 1266.50. found 1267.10.

Tris ((4-(2-O-(5-N-acetamido-3,5-dideoxy-D-glycero-α-D-galacto-2-nonulopyranosylonic acid))-2-oxoethyl-1H-1,2,3-triazol-1-yl)ethyl)amine (ME0461)

Methyl ester (25.8 mg, 14b) was dissolved in MeOH (2.5 mL) and LiOH (0.17 mL, 1.0M) solutions. The mixture was stirred at room temperature for 72 hour, followed by LCMS, neutralized with amberlite IR120, concentrated and lyophilized to give 22.0 mg (88.0%) white product. $[α]_D^{20}$ −5.3 (c 1.0 mg/mL, MeOH).

¹H NMR (400 MHz, D₂O): δ 7.68 (s, 3H), 4.47 (t, J=5.3 Hz, 6H), 3.96-4.10 (m, 3H), 3.66-3.87 (m, 18H), 3.59-3.66 (m, 3H), 3.52-3.58 (m, 3H), 3.30 (t, J=5.3 Hz, 6H), 2.99 (t, J=5.8 Hz, 6H), 2.63 (dd, $J_{3eq,4}$=4.4 Hz, $J_{3eq,3ax}$=12.7 Hz, 3H), 2.03 (s, 9H), 1.67 (t, $J_{3eq,3ax}$=12.5 Hz, 3H).

$^{13}$C NMR (100 MHz, D$_2$O): δ 175.01, 173.49, 144.82, 124.00, 100.60, 72.54, 71.68, 68.27, 68.16, 63.21, 62.55, 52.48, 51.85, 48.02, 40.20, 25.67, 22.00.

ESI-MS m/z calcd for C$_{51}$H$_{82}$N$_{13}$O$_{27}$ (M+H)$^+$ 1308.54. found 1309.29.

Biological Evaluation

Cell-Binding Assay

In order to investigate the efficiency of the newly synthesized compounds (ME0385, ME0386, ME0407, ME0408, ME0461, and ME0462) to prevent the attachment of HAdV-37 virions to HCE cells, cell-binding assays based on $^{35}$S-labeled virions were performed. Based on previous studies ME0322, sialic acid and GD1a glycan were used as reference compounds (Nilsson et al N. Nat. Med. 2011, 17, 105 and Spjut et al Angew. Chem. Int. Ed. 2011, 50, 6519). The assays were carried out (see below for further details) essentially as previously described (Arnberg et al J. Virol. 2000, 74, 42 and Arnberg et al J. Virol. 2000, 74, 7691).

In brief, $^{35}$S-labeled HAdV-37 virions were pre-incubated with or without the trivalent sialic acid derivatives, GD1a glycan and sialic acid at various concentrations. The mixtures were incubated with HCE cells and unbound virions were then washed away. Finally, the cell-associated radioactivity was counted by using a scintillation counter.

Figure 2A:
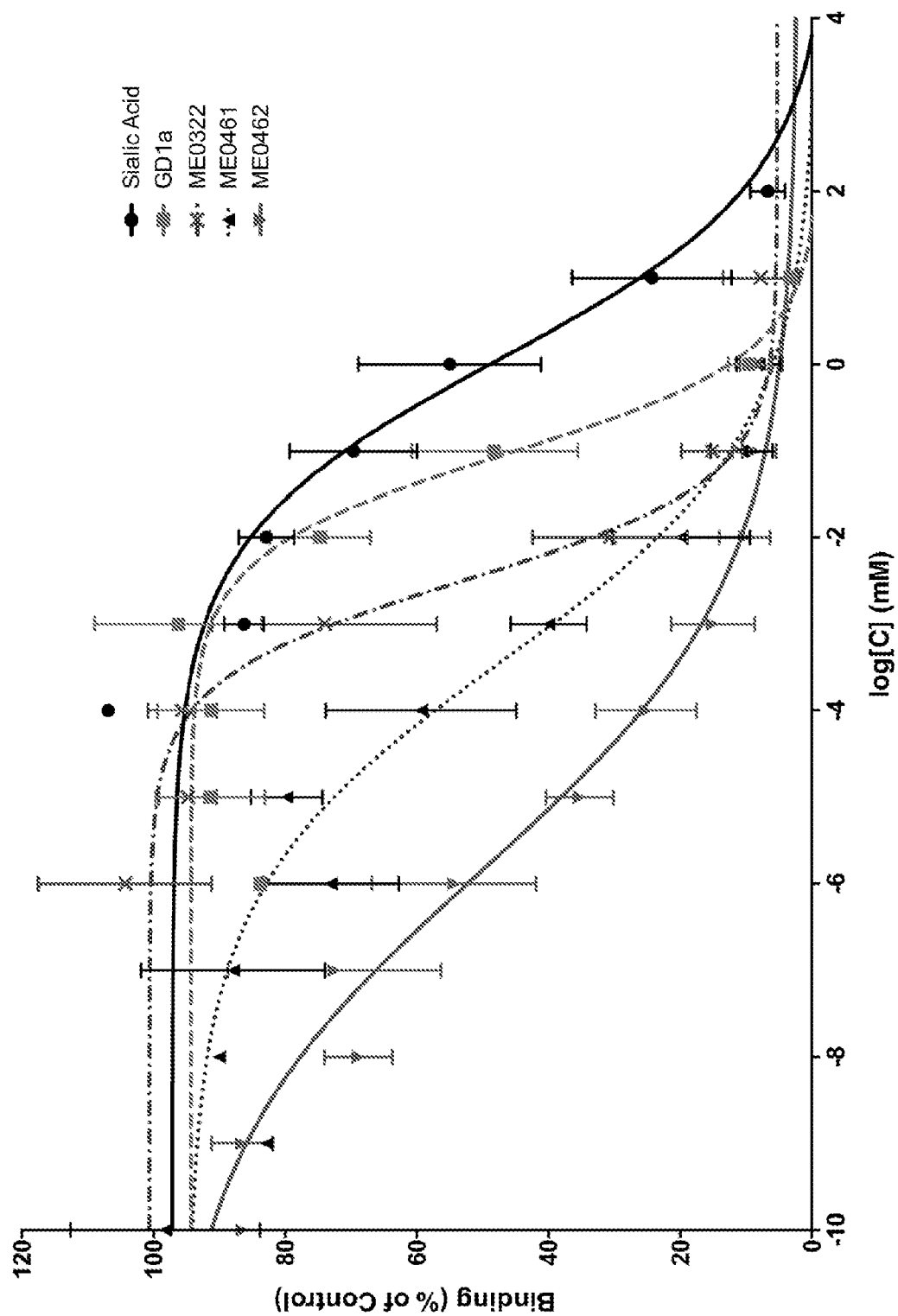

The results displayed in FIGS. 1a and 2a are highly conspicuous and thus, the attachment of HAdV-37 virions to HCE cells was dramatically hindered in the presence of the newly designed trivalent sialic acids. Indeed, the set of new compounds was evaluated and was found to be over four orders of magnitude more potent than monovalent sialic acid (IC$_{50}$=1.2 mM). Also, the new trivalent compounds were considerably more potent than the bivalent GD1a glycan (IC$_{50}$=91 μM).

Figure 2B:
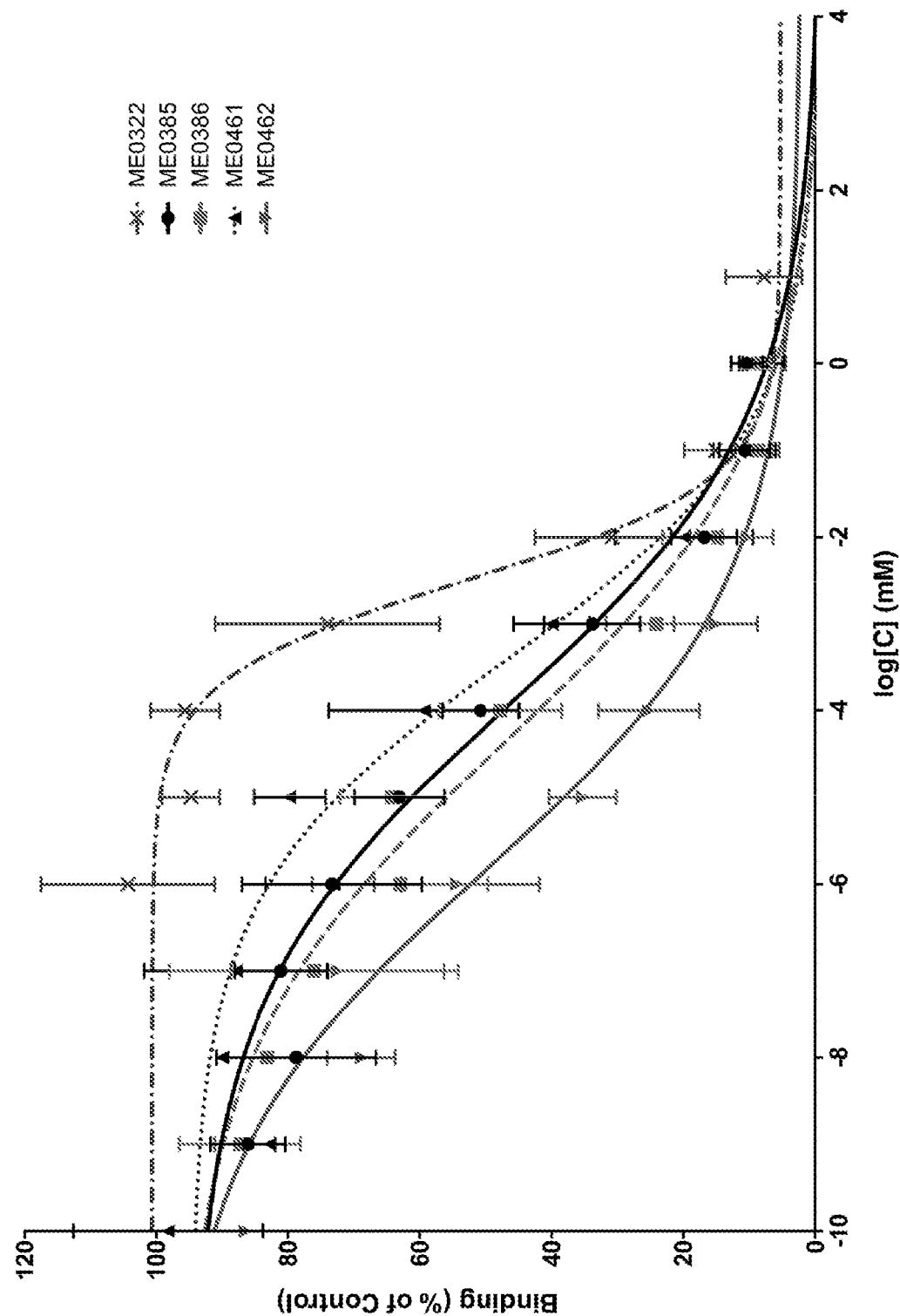

As can be seen ME0385, ME0386, and ME0461 are efficient in preventing HAdV-37 virions from HCE cells attachment with IC$_{50}$ values of 107 nM, 40 nM, and 376 nM respectively. The initial lead compound (ME0322, IC$_{50}$=3.2 μM) proved to be of lower potency. Thus, it can be concluded that compounds of the present invention are superior to the ones previously known in the art. It was further found (cf. FIG. 2b), that the analogue ME0462 (IC50=1.4 nM) was even more potent than ME0385, ME0386, and ME0461.

Finally, the N-acyl modified derivatives ME0407 and ME0408 with IC$_{50}$ values of 23.4 μM and 4.5 μM, respectively, completed the series. Unfortunately, increasing the lipophilicity of the ligands at the N-acyl moiety did not increase the potency compared to ME0385 and ME386, respectively which is supported by previous investigations (Johansson et al. J. Med. Chem. 2009, 52, 3666).

Experimental Details—Cell-Binding Assay

S-labeled HAdV-37 virions (5×10$^8$/well) were pre-incubated in binding buffer (50 μL; BB: Dulbecco's modified eagle's medium containing 1% BSA (Roche AB, Stockholm, Sweden) and HEPES (20 mM, EuroClone, Milan, Italy), pH 7.5) with or without the trivalent sialic acid derivatives, GD1a glycan or sialic acid at various concentrations (cf. FIG. 1a) in a 96-well microplate at +4° C. for 1 h. These mixtures were then added to HCE cells prepelleted (1×10$^5$/well) in a 96-well microplate. After re-suspension, the mixtures were incubated at +4° C. for 1 h. Finally, unbound virions were washed away with BB and the cell-associated radioactivity was counted by using a Wallac 1409 scintillation counter.

Infection Assay

Figure 1B:
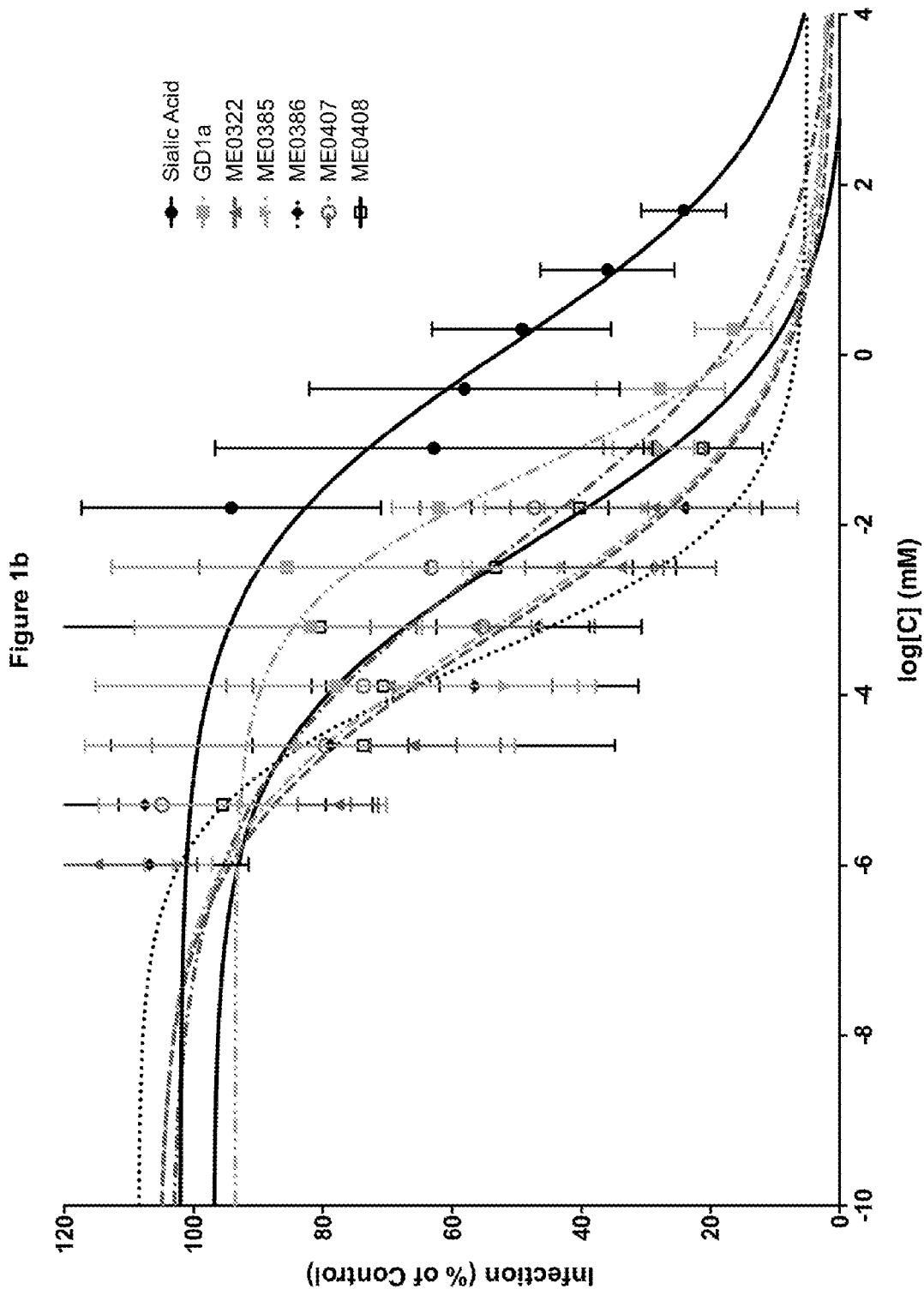

In order to confirm the results from the cell-binding assays and to further evaluate our set of compounds, infection experiments were performed (FIGS. 1b, 3a and 3b). The assays were carried out (see below for further details) essentially as previously described ((Arnberg et al. J. Virol. 2000, 74, 42 and Arnberg et al. J. Virol. 2000, 74, 7691)).

In brief, unlabeled virions were pre-incubated with or without the trivalent sialic acid derivatives, GD1a glycan or sialic acid at various concentrations. These mixtures were then added to HCE cells and incubated at +4° C. Unbound virions were washed away, the resulting mixtures were incubated at +37° C. and a synchronized infection—all virions enter the cells simultaneously—was then obtained. After 44 h of infection, the cells were rinsed, fixed, incubated with rabbit polyclonal anti-HAdV-37 antibodies prior to being washed and stained. Finally, the cells were washed and examined by immunofluorescence microscopy.

Hence, the trends from the cell-binding assays (FIGS. 1a, 2a and 2b) were confirmed in the infection experiments (FIGS. 1b, 3a and 3b). Compounds ME0386 and ME0385 prevented infection of HCE cells by HAdV-37 virions more efficiently than ME0322 with IC50 values of 118 nM and 166 nM, respectively. The half maximal inhibitory concentration of ME0322 that had previously been estimated to be 380 nM was herein calculated to be 228 nM. Also, ME0461 and ME0462 prevented infection of HCE cells by HAdV-37 virions more efficiently than ME0322. Further, also in the infection assay (cf. FIG. 3b) the analogue ME0462 (IC50=2.1 nM) was the most potent one.

Experimental Details—Infection Assay

7×10$^7$ non-labeled virions/well in 48-well plates were pre-incubated in serum free growth media (2004), with or without the trivalent sialic acid derivatives, GD1a glycan or sialic acid at various concentrations (cf. FIG. 2B) at +4° C. After 1 h, the mixtures were transferred to new 48-well plates containing 1×10$^5$ adherent HCE cells/well and incubated at +4° C. After 1 h, unbound virions were washed away with serum free growth media and the resulting mixtures were incubated with growth media containing 1% fetal bovine serum (FBS) at +37° C. After 44 h of infection, the cells were rinsed in PBS, fixed with cold (−20° C.) 99% methanol for 10 min and incubated with rabbit polyclonal anti-HAdV-37 antibodies diluted 1:200 in PBS (pH 7.4) at room temperature. After 1 h, the cells were washed in PBS and stained with FITC-labeled swine anti-rabbit IgG antibodies (Dako-cytomation, Glostrup, Denmark) diluted 1:100 in PBS for 1 h at room temperature. Finally, the cells were washed in PBS and examined in an immunofluorescence microscope (Axiovert 25, Carl Zeiss, Germany; 10× magnification).

Surface Plasmon Resonance (SPR)

Finally, ME0385, ME0386 and ME0322 were investigated in surface plasmon resonance (SPR) experiments and their respective binding affinities (Kds) for immobilized HAdV-37 fiber knobs were determined (see below for further details). SPR data corroborated well the trends from both cell binding and cell infection assays and the three compounds proved to interact with the HAdV-37 fiber knob in a one-to-one binding mode. Thus, ME0386 (Kd=69 μM) was confirmed to best interact with the HAdV-37 fiber knob, followed by ME0385 and ME0322 (Kd=76 μM and Kd=126 μM, respectively). It is also worth noting the influence of the HAdV-37 fiber knob construct on the Kd values. Similar to the binding and infection assay, ME0462 had the highest binding affinity (Kd=9.5 μM).

Experimental Details—Surface Plasmon Resonance

The kinetic measurements were performed using a surface plasmon resonance BIAcore T100 instrument. HAdV-37 knob proteins were covalently coupled to a CM5 sensorchip using the amine coupling kit (GE Healthcare), to a concentration of 14-15 ng/mm² (~15000RU). Binding of the trivalent sialic acid conjugates ME0322, ME0385 and ME0386 to the immobilized knob was performed in 10 mM HEPES, 0.15 M NaCl and 0.05% P20 pH 7.4 (1×HBS-EP+, GE Healthcare). The concentrations of trivalent sialic acid used were 400, 200, 100, 50 (twice), 25, 12.5 (twice), 6.25, 3.125, 1.56 and 0.78 µM. The binding affinities (Kds) were calculated using Biacore T100 evaluation software.

In summary, compounds of the present invention, such as ME0385, ME0386, ME0461 and ME0462, have been found to show a superior potency compared to compounds of the art, such as ME0322, in preventing an ocular infection caused by a virus, such as HAdV-37, which binds to terminal sialic residues present on the cell surface of the cell to be infected by said virus. The compounds of the present invention are thus deemed to be highly useful in the treatment of epidemic keratoconjunctivitis.

The invention claimed is:

1. A tri- or tetravalent sialic acid derivate, said derivative comprising a core moiety to which 3 groups according to formula A or B are attached

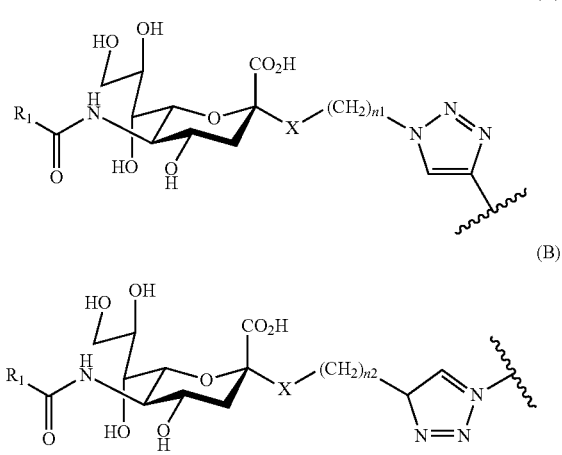

wherein
"X" is O (oxygen), NH or S (sulfur);
R1 is C1-3 alkyl;
the integer "n1" is 2 to 8;
the integer "n2" is 1 to 8; and
the waved line indicates the point of attachment to the core moiety; wherein said core moiety is a moiety according to the formula

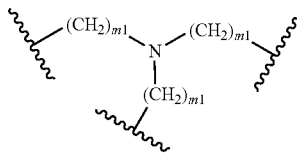

wherein
the integer "m1" is 1 to 8 if the groups attached to the core moiety are groups according to formula A;
the integer "m1" is 2 to 8 if the groups attached to the core moiety are groups according to formula B;
the waved lines indicate the point of attachment to the groups according to formula A or B;

as a free base, an acid in its non-charged protonated form, a zwitterion, a pharmaceutically acceptable addition salt, solvate, or solvate of a salt thereof.

2. The sialic acid derivate according to claim 1, wherein "X" is O (oxygen) and wherein R1 is methyl.

3. The sialic acid derivate according to claim 1, wherein the integer "n1" is 2 or 3; and the integer "n2" is 1, 2, or 3.

4. The sialic acid derivate according to claim 1, wherein said groups are groups according to formula A.

5. The sialic acid derivate according to claim 1, wherein said groups are groups according to formula B.

6. The sialic acid derivate according to claim 1, wherein the molecular weight of said derivate in its free form is 1,500 Da or less.

7. The sialic acid derivate according to claim 1, wherein the integer "m1" is 1 to 3.

8. The sialic acid derivate according to claim 7, wherein said groups are groups according to Formula A.

9. The sialic acid derivate according to claim 7, wherein said groups are groups according to Formula B.

10. The sialic acid derivate according to claim 1, wherein said sialic acid derivate is selected from the group consisting of:
   Tris ((2-O-(5-N-acetamido-3,5-dideoxy-D-glycero-α-D-galacto-2-nonulopyranosylonic acid)-2-oxoethyl-1H-1,2,3-triazol-4-yl)methyl)amine;
   Tris ((3-O-(5-N-acetamido-3,5-dideoxy-D-glycero-α-D-galacto-2-nonulopyranosylonic acid)-3-oxopropyl-1H-1,2,3-triazol-4-yl)methyl)amine;
   Tris ((2-O-(5-N-propanoylamido-3,5-dideoxy-D-glycero-α-D-galacto-2-nonulopyranosylonic acid)-2-oxoethyl-1H-1,2,3-triazol-4-yl)methyl)amine;
   Tris ((3-O-(5-N-propanoylamido-3,5-dideoxy-D-glycero-α-D-galacto-2-nonulopyranosylonic acid)-3-oxopropyl-1H-1,2,3-triazol-4-yl)methyl)amine;
   Tris ((4-(2-O-(5-N-acetamido-3,5-dideoxy-D-glycero-α-D-galacto-2-nonulopyranosylonic acid))-2-oxomethyl-1H-1,2,3-triazol-1-yl)ethyl)amine; and
   Tris ((4-(2-O-(5-N-acetamido-3,5-dideoxy-D-glycero-α-D-galacto-2-nonulopyranosylonic acid))-2-oxoethyl-1H-1,2,3-triazol-1-yl)ethyl)amine.

11. The sialic acid derivate according to claim 1, wherein said sialic acid derivate is present as a pure stereoisomer or in an anomeric mixture comprising said compound, in which anomeric mixture the α-anomer prevails.

12. A pharmaceutical composition for administration to the eye comprising a sialic acid derivate according to claim 1 and at least one pharmaceutical acceptable excipient.

13. The pharmaceutical composition according to claim 12, wherein said composition is an aqueous composition comprising 0.001 to 10 mM of the sialic acid derivate according to claim 1, said aqueous composition having a water content of at least 90 wt %.

14. The pharmaceutical composition according to claim 13, wherein said aqueous composition comprises NaCl to provide an isotonic solution.

15. The pharmaceutical composition according to claim 13, wherein said aqueous composition is buffered.

16. The pharmaceutical composition according to claim 15, wherein said aqueous composition has a pH of about 6.5 to 8.

17. A method of treating an ocular infection caused by a virus selected from the group consisting of HAdV-8, HAdV-19, HAdV-37, HAdV-53, HAdV-54, and HAdV-56, which binds to terminal sialic residues present on the cell surface of the cell to be infected by said virus in a subject in need thereof, the method comprising administering an effective amount of a sialic acid derivative according to claim 1 or a pharmaceutical composition according to claim 12 to the subject.

18. A method according to claim 17, wherein said infection is epidemic keratoconjunctivitis.

\* \* \* \* \*